(12) United States Patent
Sieck et al.

(10) Patent No.: US 7,548,317 B2
(45) Date of Patent: Jun. 16, 2009

(54) APPARATUS AND METHOD FOR ANGULAR COLORIMETRY

(75) Inventors: Peter Allen Sieck, Santa Rosa, CA (US); Joe Earle Guthrie, Sonoma, CA (US); Peter Alan Maschwitz, Sebastopol, CA (US); Clive Hilton Burton, Novato, CA (US); Vanhlacky Lucky Singhavara, Rohnert Park, CA (US); Bryan Richard Marshall, Rohnert Park, CA (US)

(73) Assignee: AGC Flat Glass North America, Inc., Kingsport, TN (US)

( * ) Notice: Subject to any disclaimer, the term of this patent is extended or adjusted under 35 U.S.C. 154(b) by 207 days.

(21) Appl. No.: 11/418,062

(22) Filed: May 5, 2006

(65) Prior Publication Data

US 2007/0258093 A1 Nov. 8, 2007

(51) Int. Cl.
*G01N 21/55* (2006.01)
(52) U.S. Cl. ....................................................... 356/445
(58) Field of Classification Search ........................ None
See application file for complete search history.

(56) References Cited

U.S. PATENT DOCUMENTS

2002/0171840 A1* 11/2002 Davis ......................... 356/445
2003/0020917 A1* 1/2003 Mundt et al. ................. 356/446

* cited by examiner

*Primary Examiner*—Michael P Stafira
(74) *Attorney, Agent, or Firm*—Oblon, Spivak, McClelland, Maier & Neustadt, P.C.

(57) ABSTRACT

An apparatus for measuring the reflectance properties of an object having a front reflecting surface and at least one back reflecting surface. The apparatus includes a sample stage for placement of the object, a light source, a detector configured to detect reflected light from the object, and a positioning device configured to provide a plurality of angular positions for the light source and the detector relative to the object on the sample stage such that incident light on the object is specularly reflected towards the detector and the reflected light received at the detector includes a front surface reflection from the object and at least one back surface reflection from the object. The method includes illuminating the object at varying angles of incidence, collecting reflected light from the front and back reflecting surfaces of the object at respective specularly reflected angles, wavelength resolving the reflected light into a color spectrum, and analyzing an intensity of the color spectrum as a function of wavelength.

28 Claims, 22 Drawing Sheets

APPARATUS AND METHOD FOR ANGULAR COLORIMETRY

FIELD OF THE INVENTION

The invention relates to an apparatus and method for angular colorimetry with use in fields such as architectural glass panels.

BACKGROUND OF THE INVENTION

Energy efficient coatings are becoming increasingly used on architectural and automotive glass and in other applications. Their use is progressively mandated by government standards and the coatings are becoming quite sophisticated as the specifications they must meet for control of solar transmission, infrared transmission and heat retention become ever more demanding.

Indeed, in order to meet the demands for improved energy efficiency, it has been found necessary to deposit at least some of the coatings as multilayer interference stacks. (ref. *Coated Glass Applications and Markets*, R. Hill and S. Nadel, published by BOC Coating Technology, Fairfield Calif., 1999, the entire contents of which are incorporated herein by reference). These stacks have a specific reflectance color when viewed at near-normal incidence. Such coated glass is invariably used as part of a double-paned window unit consisting of two lights. The lights are sealed into the window frame with a dry gas occupying the space between the lights. The coated surface of architectural glass is usually on the second surface of such a double-paned unit if the surfaces are counted from the solar side inward. The glass of the exterior light may be tinted and, as already noted, the coatings themselves usually have some color.

When such double-paned windows (known to the trade as insulated glass units or IGUs) are used as the external cladding of a large multi-story building, the architect and others wish to see a uniform reflected color from all angles. Unfortunately, for reasons well known to the designers of multilayer coating stacks, the reflectance color of such stacks can change quite perceptibly with viewing angle. If due attention is not paid to this aspect the color change can be quite dramatic and unacceptable. This change in color, as a function of viewing angle, is referred to herein as the angular color variation.

When windows are viewed from the exterior of a building, the angular color variation is more noticeable under light from cloudy sky conditions. The illumination from a cloudy sky is randomly polarized light and its energy is fairly evenly distributed through the visible spectrum (white light). These two light characteristics enhance the perception of reflected color and reflected color change with angle in fenestration products.

The color of light reflected from windows perceived by a viewer is the sum of reflections from all the reflecting surfaces contained within the window unit.

Specular reflections off any surface such as those within a window unit are partially polarized if viewed from any angle other than normal incidence. It is well known in the field of optics that polarization effects increase with reflected angle until the Brewster angle is reached. Polarization of reflected light then tends to decrease beyond the Brewster angle until at grazing incidence, polarization effects approach zero. The human eye is typically insensitive to polarization and is able to discern color free of polarization error.

In many instances, the control of angular color variation is managed by visual inspection against a limited number of samples. The chief disadvantage of this method is that it relies on subjective judgment of a color match which is often perceived differently by different inspectors in part because about 5% of the male population has some red/green color vision deficiency.

SUMMARY OF THE INVENTION

One object of the present invention is to provide a spectral reflectance apparatus which overcomes the problems residing in the prior art.

Another object of the present invention is to provide a spectral reflectance apparatus which can provide the angular color variation data required by the glass coating and similar industries in a rugged and cost-effective form and which is suitable for use as a quality control tool as well as for coating or architectural window development.

Various of these and other objects are provided in certain embodiments of the present invention.

In one embodiment of the present invention, there is provided an apparatus for measuring the reflectance properties of an object having a front reflecting surface and a back reflecting surface. The apparatus includes a sample stage for placement of the object, a light source configured to emit white light, a detector configured to detect reflected light from the object, and a positioning device configured to provide a plurality of angular positions for the light source and the detector relative to the object on the sample stage such that incident light on the object is specularly reflected towards the detector and the reflected light received at the detector includes a front surface reflection from the object and at least one back surface reflection from the object.

In one embodiment of the present invention, there is provided a method for measuring the reflectance properties of an object having a front reflecting surface and at least one back reflecting surfaces. The method includes illuminating the object at varying angles of incidence, collecting reflected light from the front and back reflecting surfaces of the object at respective specularly reflected angles, wavelength resolving the reflected light into a color spectrum, and analyzing an intensity of the color spectrum as a function of wavelength.

It is to be understood that both the foregoing general description of the invention and the following detailed description are exemplary, but are not restrictive of the invention.

BRIEF DESCRIPTION OF THE DRAWINGS

A more complete appreciation of the present invention and many attendant advantages thereof will be readily obtained as the same becomes better understood by reference to the following detailed description when considered in connection with the accompanying drawings, wherein.

DETAILED DESCRIPTION OF THE INVENTION

In order to quantify the problem of angular color variation, to aid in the development of coatings with less angular color variability, and to ensure that angular color variability standards are met in production, it is necessary to be able to measure the total reflectance color of the coated glass. The invention in one embodiment provides a tool for an objective measurement of the angular color variability.

Gonio-spectrophotometers, multi-angle calorimeters and gonio-colorimeters are conventional instruments used for example in the paint industry where considerable effort has been put into developing such instruments. In particular, the automotive paint industry has used such instruments to analyze the color of paint in which metallic particles and mica flakes and particles including interference layer stacks have been included to produce metallic glitter and pearl effects which vary with viewing angle.

However, these and various other instruments are limited in that these instruments are not designed to capture reflected light from both a first surface and a second surface of a translucent or semi-transparent object (such as for example a coated architectural glass having a substantial thickness in excess of several millimeters.

Figure 1:
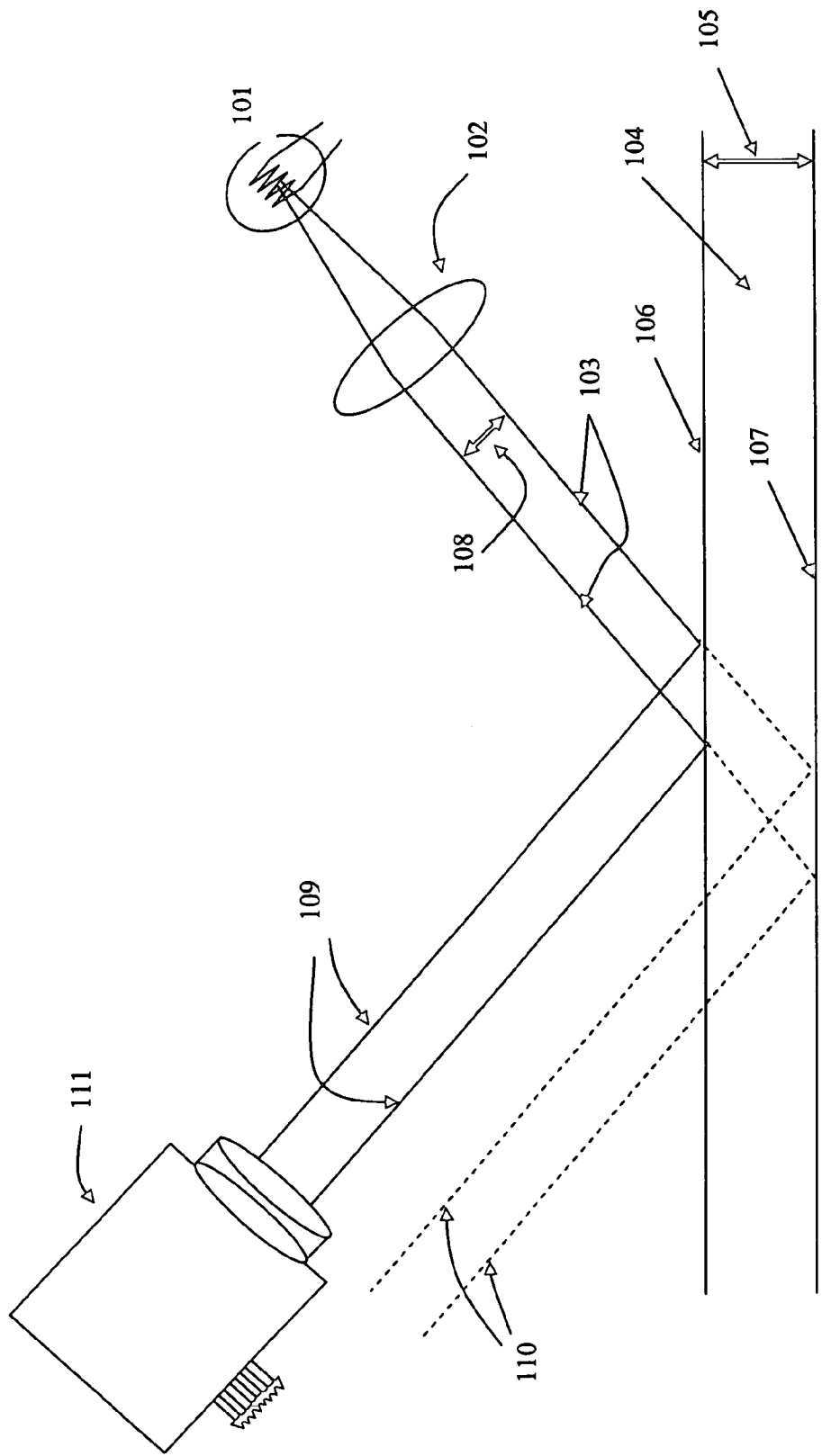
FIG. 1 is a schematic illustration of a conventional instrument recording reflected light from a glass plate.

Referring now to the drawings and more particularly to FIG. 1, FIG. 1 illustrates the problem faced by a conventional instrument. Light from a source 101 is collimated by lens 102 and the resulting collimated beam 103 is incident on a glass object 104 of thickness 105. The object has first surface 106 and second surface 107. The collimated beam has a diameter w (108). Specularly reflected light beams of equal diameter 109 and 110 travel towards a detector 111 which is usually sized so as to collect little more than the entirety of the first surface reflected beam 109. The second surface reflected beam 110 is either not collected at all or only partially collected so the instrument does not provide an accurate measurement of the total specular reflectance of both surfaces. Indeed, some instruments are designed specifically to reject the second surface reflection, and in others the partial second surface reflection collected is regarded as a nuisance and strategies are employed to negate it by painting the second surface black or roughening it or doing both. The second surface reflection in some instruments is sometimes eliminated using a specially wedged sample having an angle of at least several degrees between front and back surfaces so that the back surface reflection is directed away from the detector.

Figure 2:
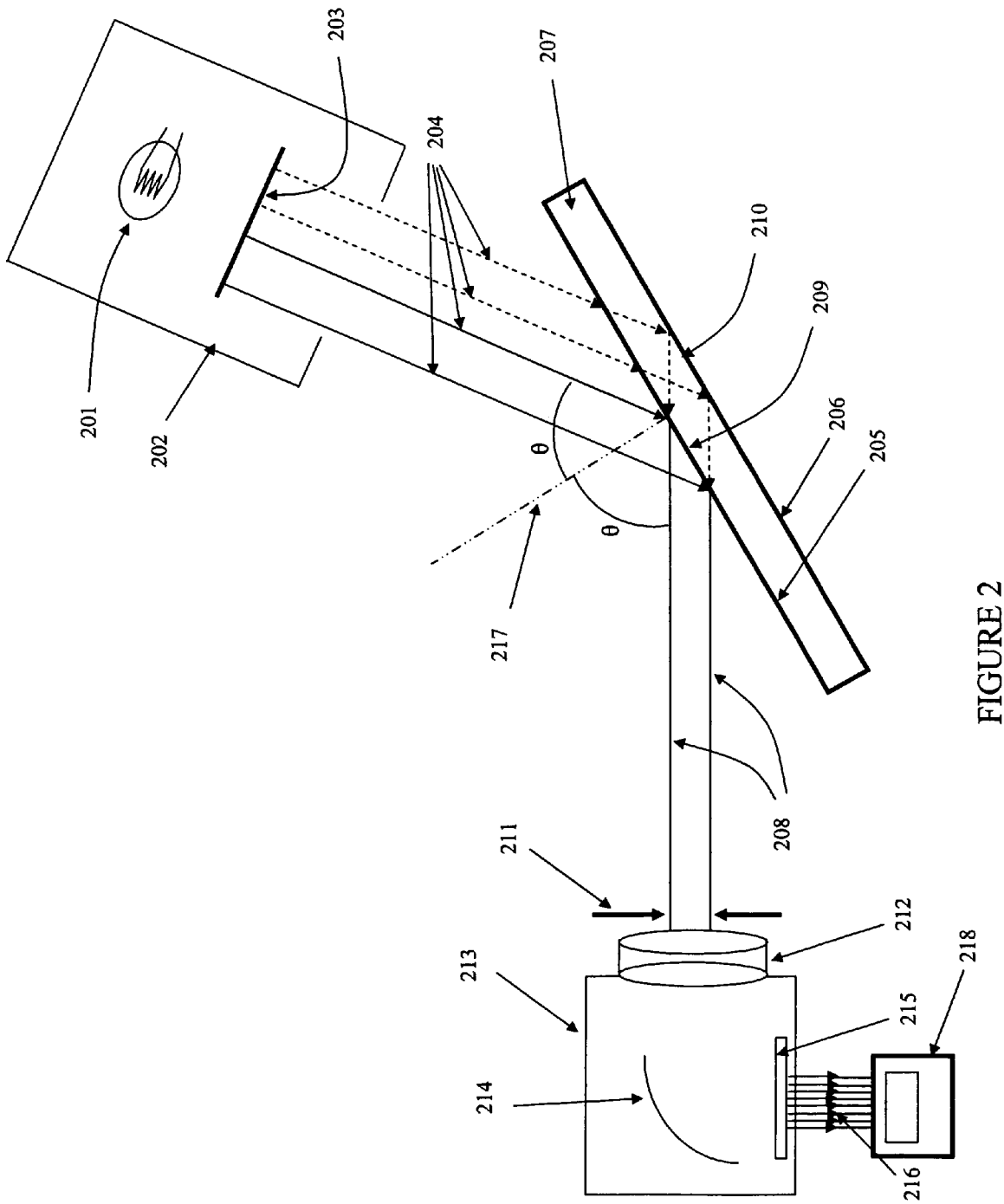
FIG. 2 is a schematic illustrating one embodiment of the present invention in which both front and back surface reflections from a glass plate are measured.

FIG. 2 is a schematic illustrating one embodiment of the present invention in which both front and back surface reflections are measured from a glass plate, as shown by the optical diagram depicted in FIG. 2. The apparatus shown in FIG. 2 includes a lamp 201 in an integrating enclosure 202 which is coated internally with a diffusely reflecting white material such as for example barium sulfate or SPECTRALON™ as sold by Labsphere. Light from the enclosure 202, after multiple reflections in the enclosure 202, falls on surface 203 which is also coated on both sides with the diffusely reflecting white material. Light rays 204 from the surface 203 falling on front surface 205 of an object 207 (e.g. a sample of architectural glass), are partially reflected, and are partially transmitted to the back surface 206 of the object 207 from which a second reflection occurs. As shown in FIG. 2, specularly reflected rays 208 from equal areas 209 and 210 on the front and back surfaces, respectively, are selected by aperture 211 and are transmitted by a lens system 212 to a detector 213 which incorporates a wavelength dispersive mechanism 214, a photodiode array 215, and a signal transmission device 216 which transmits the spectral data from the photodiode array 215 to a computing device 218 for manipulation of the spectral data to provide calibrated spectra and color data.

For specular reflection, the angle between the surface normal 217 and the incident beam 204 (the angle of incidence) equals the angle between the surface normal and the reflected beam 208 (the angle of reflection θ). In order to ensure that the reflected beam is always directed along the same path to the photoreceptor for all angles of incidence, the sample or object 207 should be rotated at half the angular rate of the arm holding the light source. This is because a change in the angle θ by rotating the light source 201 for example towards the detector 213 will have to be accommodated by the object 207 being rotated by θ/2 in order that the reflections from surfaces 209 and 210 will travel in the same direction to be received by the aperture 211 and the detector 213. The front and back reflections from surfaces 209 and 210, respectively, are nominally parallel, as shown. The detector in one embodiment of the present invention has a narrow angle of acceptance (e.g., approximately 1-5 degree) that restricts the light to that which has been specularly (as opposed to diffusely) reflected.

Figure 3:
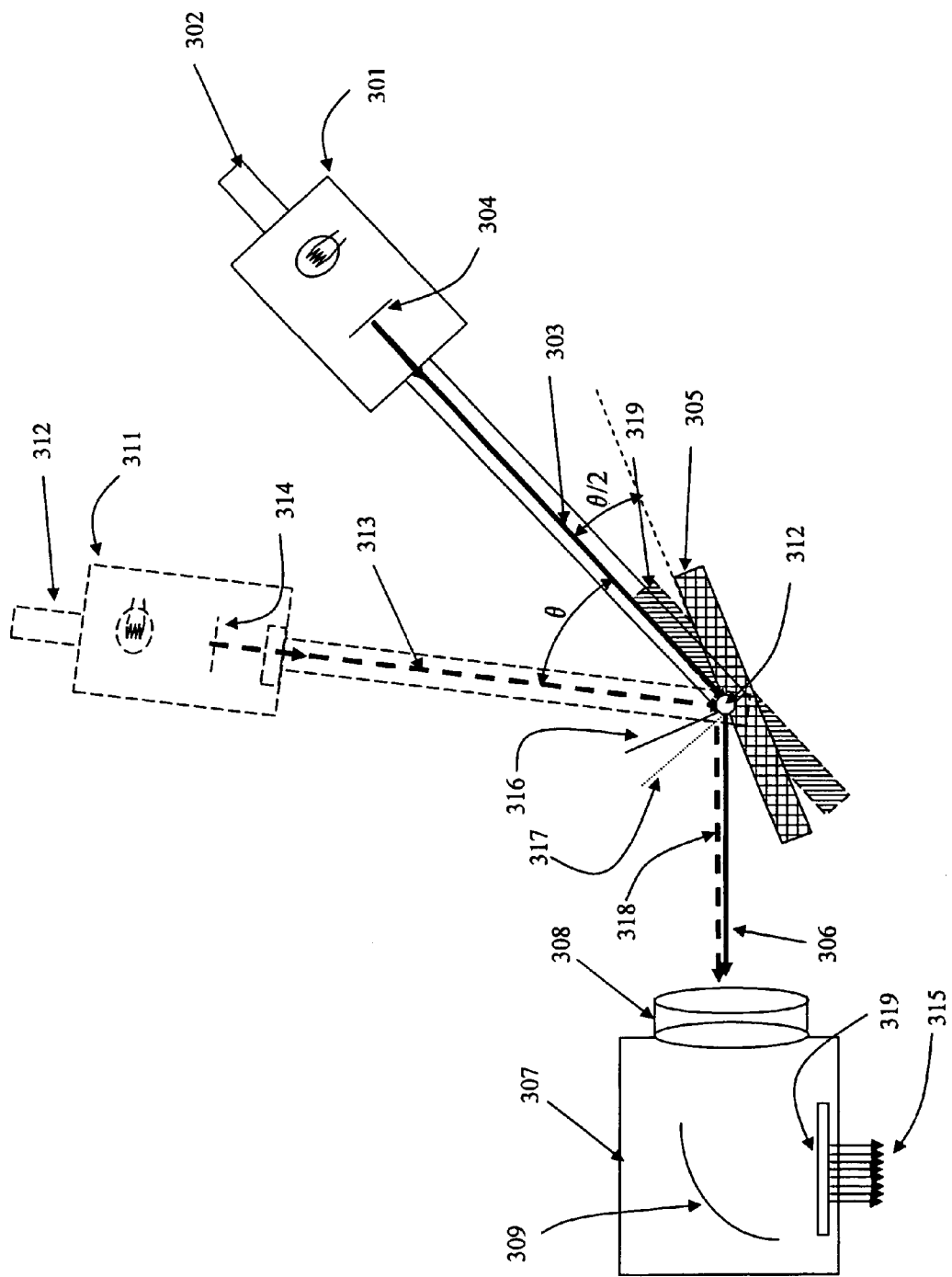
FIG. 3 is a schematic illustration of the movement of the optical source and the sample in a controlled manner according to one embodiment of the present invention.

FIG. 3 is a schematic illustration of the movement of the optical source and the sample in a controlled manner according to one embodiment of the present invention. In this embodiment, the rotational relationship is accomplished by a novel goniometric arrangement. On the right hand side of FIG. 3, the light source 301 is shown in its first position (solid lines) on arm 302. Light rays 303 from the diffusely illuminated white surface 304 impinge on the sample shown in its first position 305, and light rays reflected from both its front and back surfaces, indicated by the solid line 306 are directed towards the spectrally selective detector 307 shown in this example as including a lens system 308, an optical grating 309, a linear diode array 320 (acting as individual photodetectors) and a digital output 315.

A second position for the light source and arm is shown at 311 and 312, respectively, (dotted lines). Light rays 313 (heavy dashed line) from the diffuse surface 314 in this second position impinge on the sample (or object) 319 which has been rotated only half the angular rotation of the arm from its first position. This ensures that reflected rays 318 (heavy dashed line) from both back and front surface of the sample 319 in its second position are directed towards the detector 307. The normal to the sample is indicated at 316 and 317 in the first and second position of the sample, respectively. The angle between these two normals is half the angular rotation of the arm from its first position to the second position.

Figure 4A:
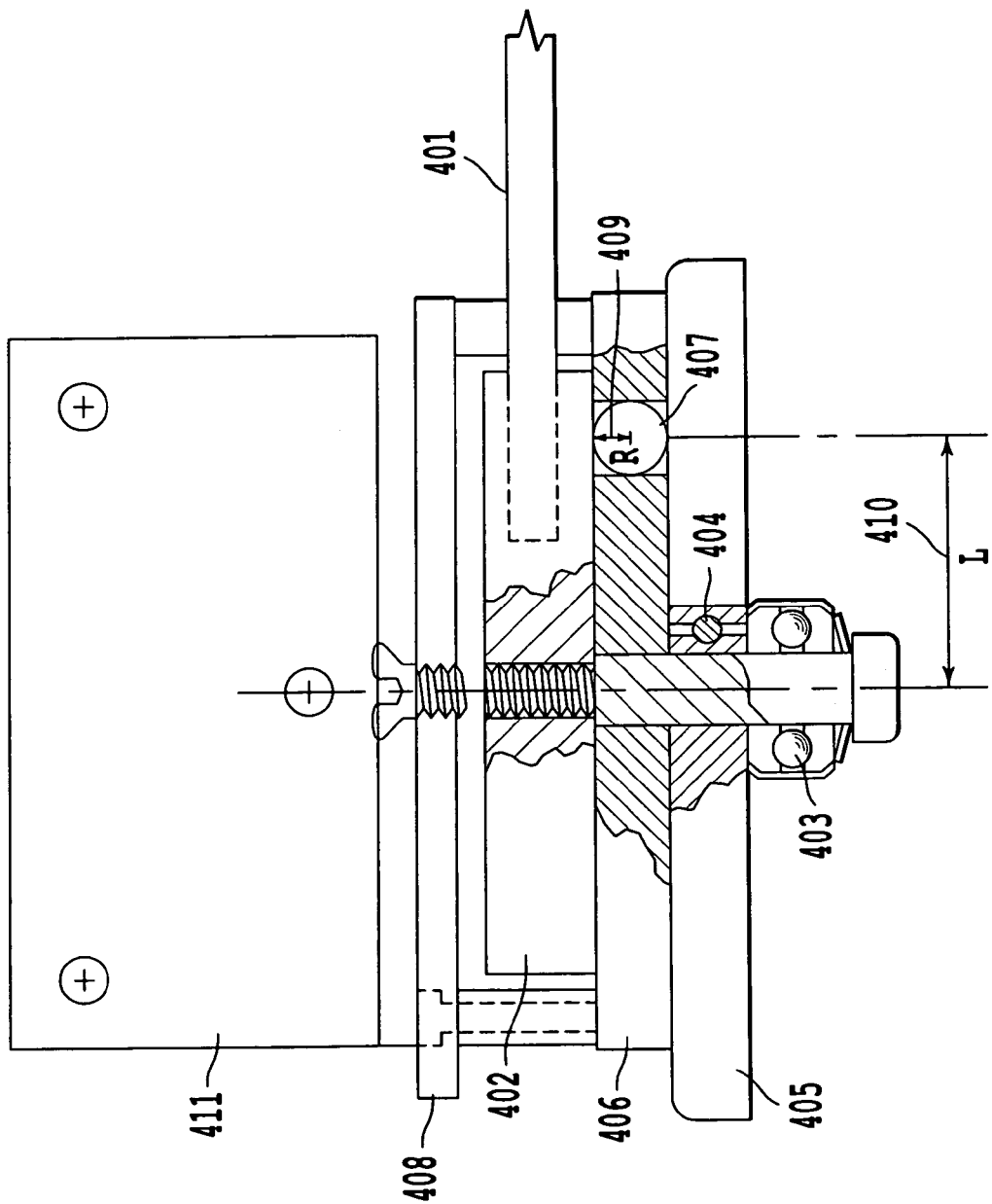
FIG. 4A is a schematic of a novel goniometric arrangement of the present invention providing the controlled movement shown in FIG. 3.

FIG. 4A is a schematic of a novel goniometric arrangement of the present invention providing the controlled movement shown in FIG. 3. The arm 401 in FIG. 4A which holds the light source is fixed to a first rotatable plate 402 which rotates on an axle 404 mounted by way of bearing 403 to a fixed plate 405. Between the fixed plate 405 and the first rotatable plate 402 is a second rotatable plate 406. The ball bearing 407 contacts both the first rotatable plate 402 and fixed plate 405. As the first rotatable plate 402 is rotated, the ball bearing 407 rolls. This rolling motion of the ball bearing 407 on a contact surface with the fixed plate 405 pushes the second rotatable plate 406 in the same direction as the motion of the first rotatable plate 402. The effect of this arrangement is that the first rotatable plate 402 attached to the light source arm 401 rotates in the same angular direction at twice the angular rate of rotatable plate 406 to which the sample holder is fixed.

To understand this effect better, consider the centroid of ball bearing 407 in the race. As the ball rotates one full revolution, the centroid moves an arc distance $s=2\pi R$ with reference to the fixed plate 405 (where R is the radius 409 of a ball bearing in the ball race). The second rotatable plate 406 containing the ball race 407 must therefore move an equivalent angle s/L where L is the radius 410 of a contact point of the ball bearing from the axis of the axle 403.

The contact point between the ball bearing 407 and the first rotatable plate 402 must also move a distance s relative to the centroid of the ball race. Thus for one revolution of the ball bearing 407, the first rotatable plate 402 moves a total arc length of 2s relative to the fixed plate 405, i.e. the first rotatable plate moves at twice the angular rate of the second rotatable plate, as required.

The sample holder 411 is itself attached to the sample holder mount 408 by attachment mechanism (not shown) which allows the sample holder to be adjusted, with three degrees of freedom, for alignment purposes.

In one embodiment of the present invention, the detector is a Photo Research PR650 SPECTRA SCAN™ device used as a spectrally selective photodetector. This detector has the advantage of providing a focusing lens and a visible circular graticule black spot in the eyepiece which indicates the acceptance area of the photodetector within the substantially larger field of view.

The setup procedure for the SPECTRA SCAN™ device or other detector instrument includes an alignment procedure to ensure that the axis of rotation of the goniometer intersects the surface of the sample and that the detector device is focused on the diffusely illuminated surface 304 in FIG. 3. When viewed through the detector device, the reflected light from the front and back surfaces of a coated glass sample forms two images in the eyepiece which are separated by a distance proportional to the thickness of the glass and also dependent on the angle of incidence. For architectural glass with energy efficient coatings, the images are usually of a different color and the area of overlap is brighter than either of the images alone. (See FIG. 11 later).

Other embodiments of the present invention incorporate the ability to automate the measurement by moving the light source and sample by computer control such as for example computer control of stepper motors and the like so that the measurements can be completely automatic after the initial setup and insertion of a sample.

Such embodiments may include the ability to measure angular color on line in a glass coating plant or in the field—for instance on an existing building to match window units which need to be replaced due to damage or deterioration. An on line version of the instrument may incorporate optical systems which enable the measurement of angular color at several locations across, for instance, coated glass in a glass coating plant.

The invention is useful as an economic alternative to expensive variable angle spectroscopic ellipsometer (VASE) instruments in that angular color colorimeter of the present invention can provide some of the same type of information about the thicknesses of layers in a coating stack for development and process control purposes. For example, information from angular measurements could be used to reverse engineer the thickness of the center dielectric layer in a double low-e architectural coating which is perhaps too thick. For instance, the sputter machine power levels to the cathodes depositing the center layer would be adjusted, in this case reduced, to bring the thickness back to a nominal value. The information provided could be integrated into an on-line process control system with feedback via an artificial intelligence system such as a fuzzy logic system or learning neural network system or a simple PID loop.

Experienced coating plant operators and coating design scientists develop rules for adjusting coating processes based on particular deviations of a spectral reflectance or transmittance plot from the ideal. Traditionally the spectral reflectance and transmittance plots have been taken only at near normal incidence. The angular calorimeter of the present invention allows the presentation of spectral reflectance plots at a variety of angles and therefore provides additional information, along with the angular color plot, which an experienced operator/scientist can learn to use to adjust the process.

It is well known by manufacturers of fenestration products that the preferred reflectance color for windows is in the neutral to slightly blue green range. Windows showing red, yellow, or purple reflectance colors are not as popular in the marketplace. It is also preferred that if a fenestration product changes color with viewing angle, at no angle should the reflection appear red, yellow, or purple. For the majority of window constructions, the reflection color seen from the exterior of a building is known as the glass side reflection. In most window construction incorporating insulated glass units, the outermost light is the low emissivity coated light and the thin film coating is on the interior side of this outer light. Therefore, in this construction, the most noticeable color on a window viewed from the building exterior is the glass side reflection color.

One type of coating commonly applied to architectural glass is known as a low emissivity or heat reflecting coating. These are typically multilayer thin film stacks consisting of alternating layers of dielectric and an infrared reflective metal such as silver. Other layers may be present such as protective or nucleation layers around the silver. These glass coatings commonly include one to three layers of silver. When these stacks contain two or more layers of silver separated by dielectric interference layers, angular color variation may be large enough to create a product unacceptable in the marketplace. If the layer materials of these thin film stacks are controlled accurately for layer thickness and optical properties, various optical and mechanical properties including angular color variation may be held within acceptable limits. The angular color measurement device of this invention may be used to determine if layer thicknesses and optical properties are correct. Tuning of the deposition process may be done based on the readings from the angular color measurement device. The tuning process may be done manually or by automatic feedback process control.

Through the use of computer simulation of thin film stacks and practical coating experience, correlations may be made between angular color measurements and layer thicknesses and optical properties.

EXAMPLE 1

Two low emissivity stack designs are given in the following table along with the layer thickness change from Design A to Design B.

| | Layer Thickness in nanometers | | |
|---|---|---|---|
| Layer Material | Design A | Design B | A to B Thickness Difference |
| SiAlOxNy | 24.6 | 26.2 | 1.6 |
| NiCr metal | 5.5 | 4.8 | −0.6 |
| NiCrOx | 1.0 | 1.0 | 0.0 |
| Ag | 13.0 | 13.0 | 0.0 |
| ZnO | 6.0 | 6.0 | 0.0 |
| SiAlOxNy | 56.0 | 60.0 | 4.0 |
| NiCr metal | 8.0 | 8.0 | 0.0 |
| NiCrOx | 2.0 | 2.0 | 0.0 |
| Ag | 10.5 | 10.5 | 0.0 |
| ZnO | 10.0 | 10.0 | 0.0 |
| SiAlOxNy | 12.3 | 15.1 | 2.8 |
| Glass Substrate (thickness in mm) | 3.2 | 3.2 | 0.0 |

When single light, normal incidence color readings are taken on these designs, both show similar numbers and either would be acceptable in the marketplace.

| | Normal Incidence Color (8.5 degrees) | | | |
|---|---|---|---|---|
| | | a* | b* | L* |
| Design A | Transmission | −3.26 | −2.90 | 70.25 |
| | Glass Side Reflection | −1.85 | −3.79 | 40.77 |
| | Coated Side Reflection | −8.37 | 0.83 | 26.42 |
| Design B | Transmission | −3.04 | −2.04 | 72.14 |
| | Glass Side Reflection | −1.79 | −3.90 | 41.23 |
| | Coated Side Reflection | −10.31 | 5.02 | 26.57 |

When glass side reflection color readings at various angles are taken from these same coatings, Design A is shown to be red in appearance at higher angles of incidence. When the a* color measurement reaches a value greater than 1, the appearance is generally considered too red to be desirable. The layer thickness corrections in Design B result in a high angle of incidence appearance that does not become excessively red. At an angle of incidence of 75°, the a* value in Design B remains below 1.

Figure 4B:
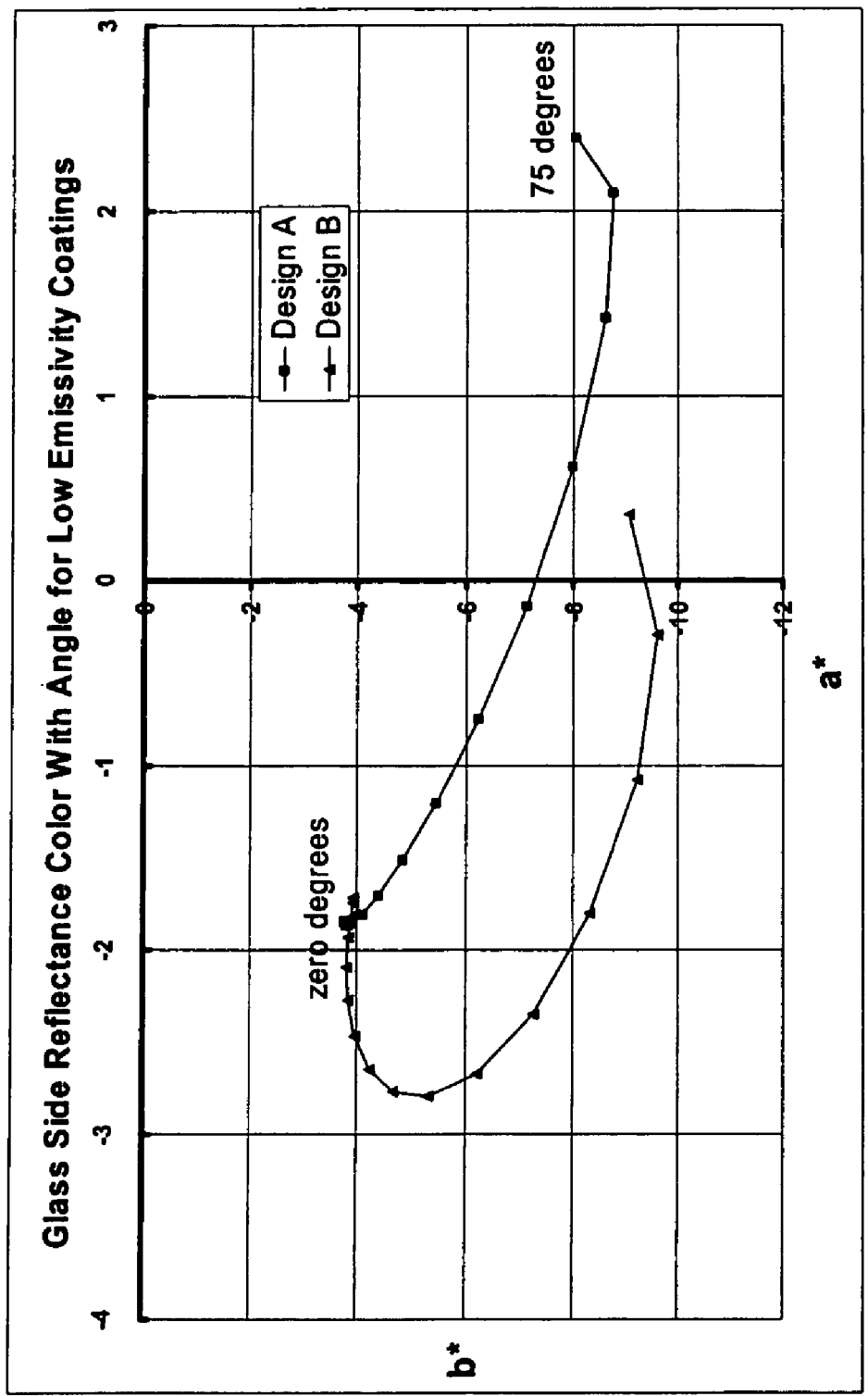
FIG. 4B is a graph that shows the glass side reflection angular color variation of a single light of low emissivity coated glass.

FIG. 4B is a graph that shows the glass side reflection angular color variation of a single light of low emissivity coated glass. The angular color readings are shown from 0.0 to 75 degrees in 5 degree increments. At the 0.0 degree starting point, both reflectance colors are approximately equal and are in the preferred blue-green range. At angles of incidence greater than 65 degrees, Design A becomes excessively red. Together with the results of optical thin film stack modeling, this knowledge can be embedded in an artificial intelligence system such as a fuzzy logic or neural network system so that the process can be automatically controlled by use of a suitable software/hardware interface between the angular colorimeter (and other measurement devices) and the deposition equipment in which such parameters as the power and gas flows can be adjusted to keep the process and measurable product parameters within acceptable limits.

Figure 18:
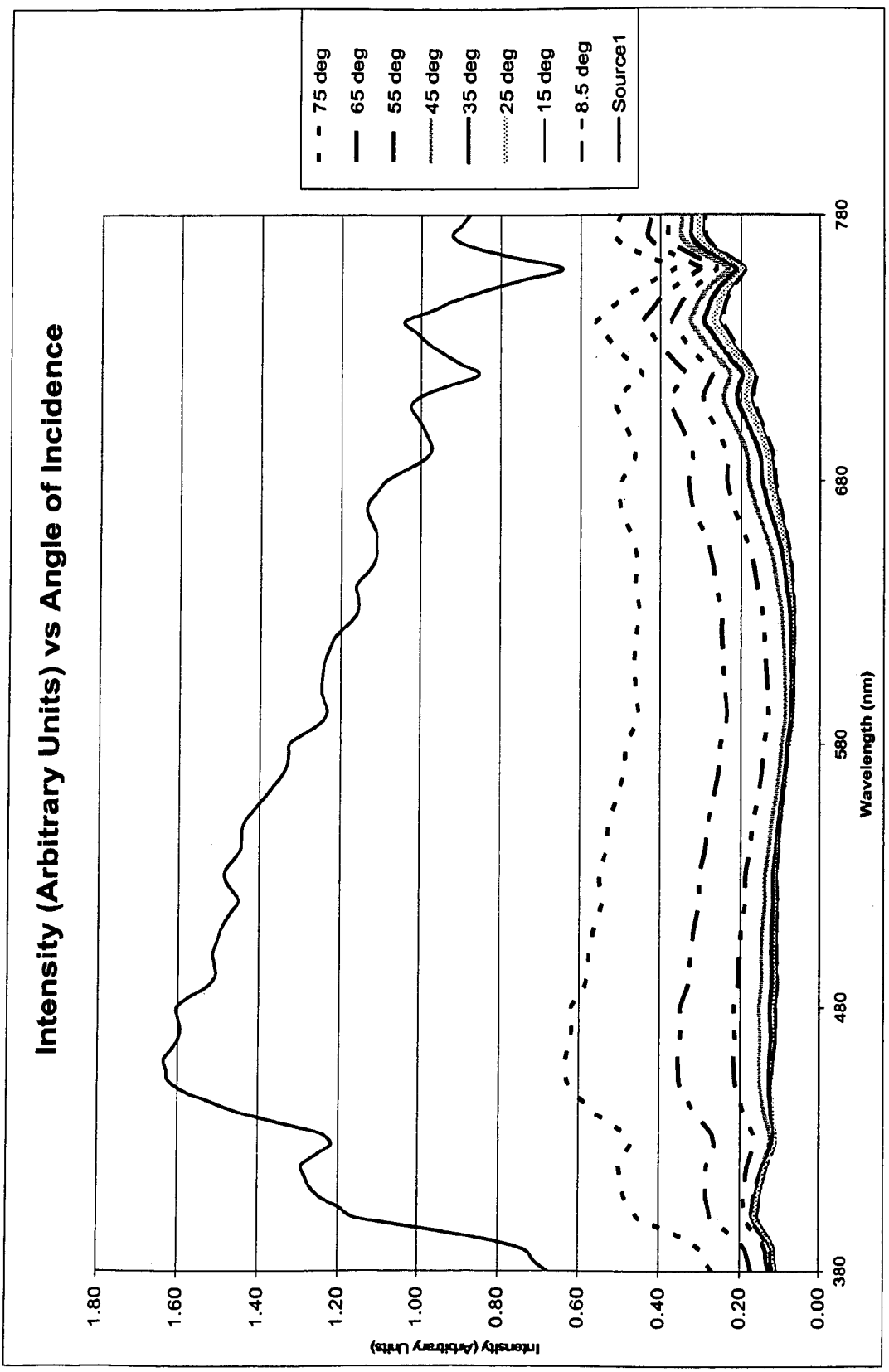
FIGS. 18 and 19 are raw spectra and the ratioed spectra (representing % Reflectance), respectively, from an angular colorimeter of the present invention.
Figure 19:
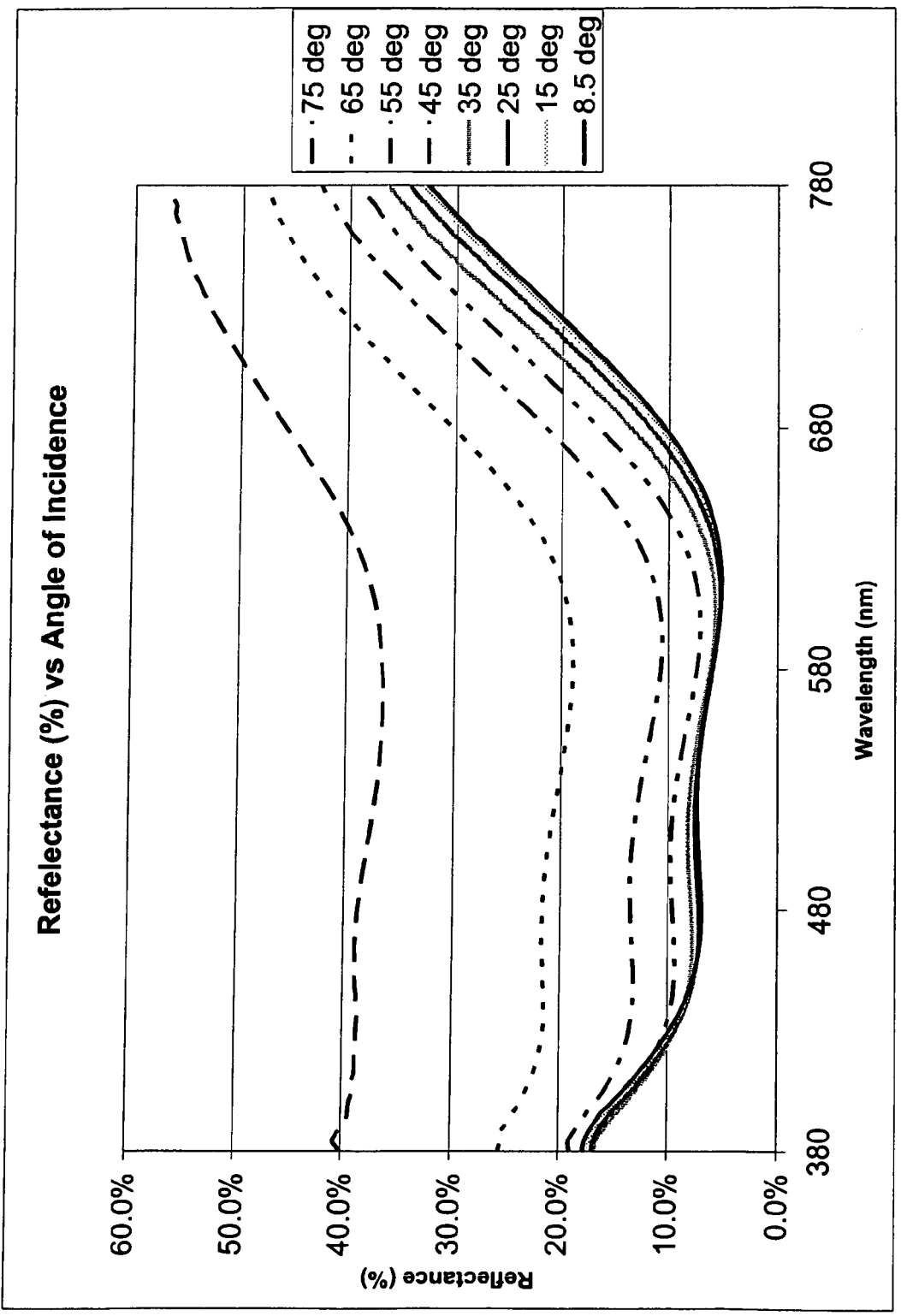

In the case of a neural network system the angular color data along with other product parameters would be fed to the neural network along with the associated process parameters so that the neural network can "learn" the best connections between the network inputs and outputs in order to control the process. FIGS. 18 and 19 show raw spectra out of the PR650 and the ratioed spectra (representing % Reflectance), respectively.

Figure 5:
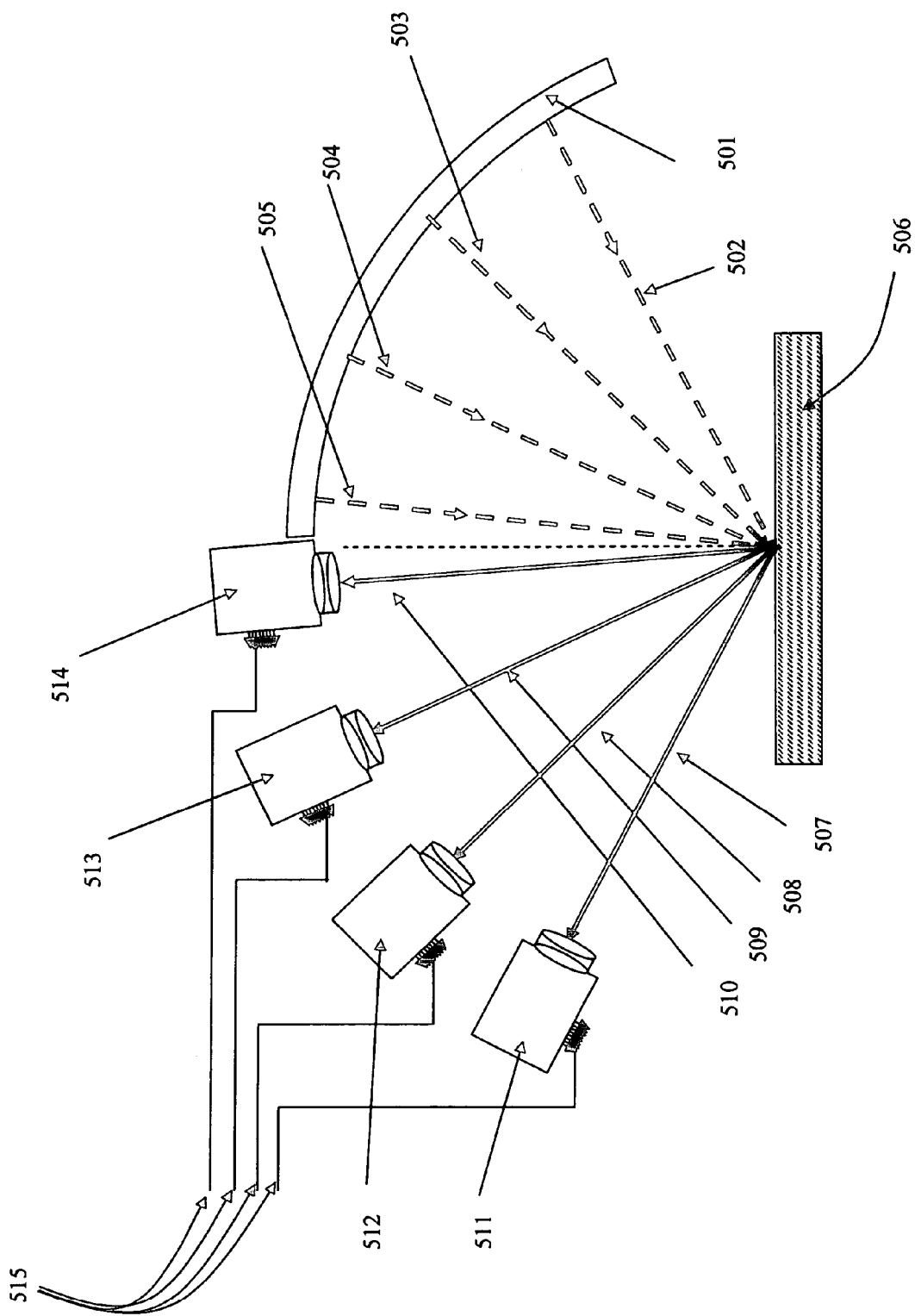
FIG. 5 is an optical schematic of another embodiment of the angular colorimeter of the invention utilizing an extended light source and a plurality of detectors.

FIG. 5 is an optical schematic of another embodiment of the angular colorimeter of the invention utilizing an extended light source and a plurality of detectors. In FIG. 5, the light source 501 is extended so that it subtends a substantial angle (e.g., 30 to 80 degrees) as measured from the center of rotation of the goniometer. Light travels along paths 502, 503, 504, 505 to sample 506 where it is specularly reflected (from both back and front surface of sample 506) along paths 507, 508, 509, 510 to detectors 511, 512, 513, 514, respectively. In this embodiment, each of the detectors selects just that light which has been specularly reflected from the sample 506 and falls within the acceptance aperture of the detector. Signal lines 515 send information to a computing device for manipulation of the spectrum from each detector.

Figure 6:
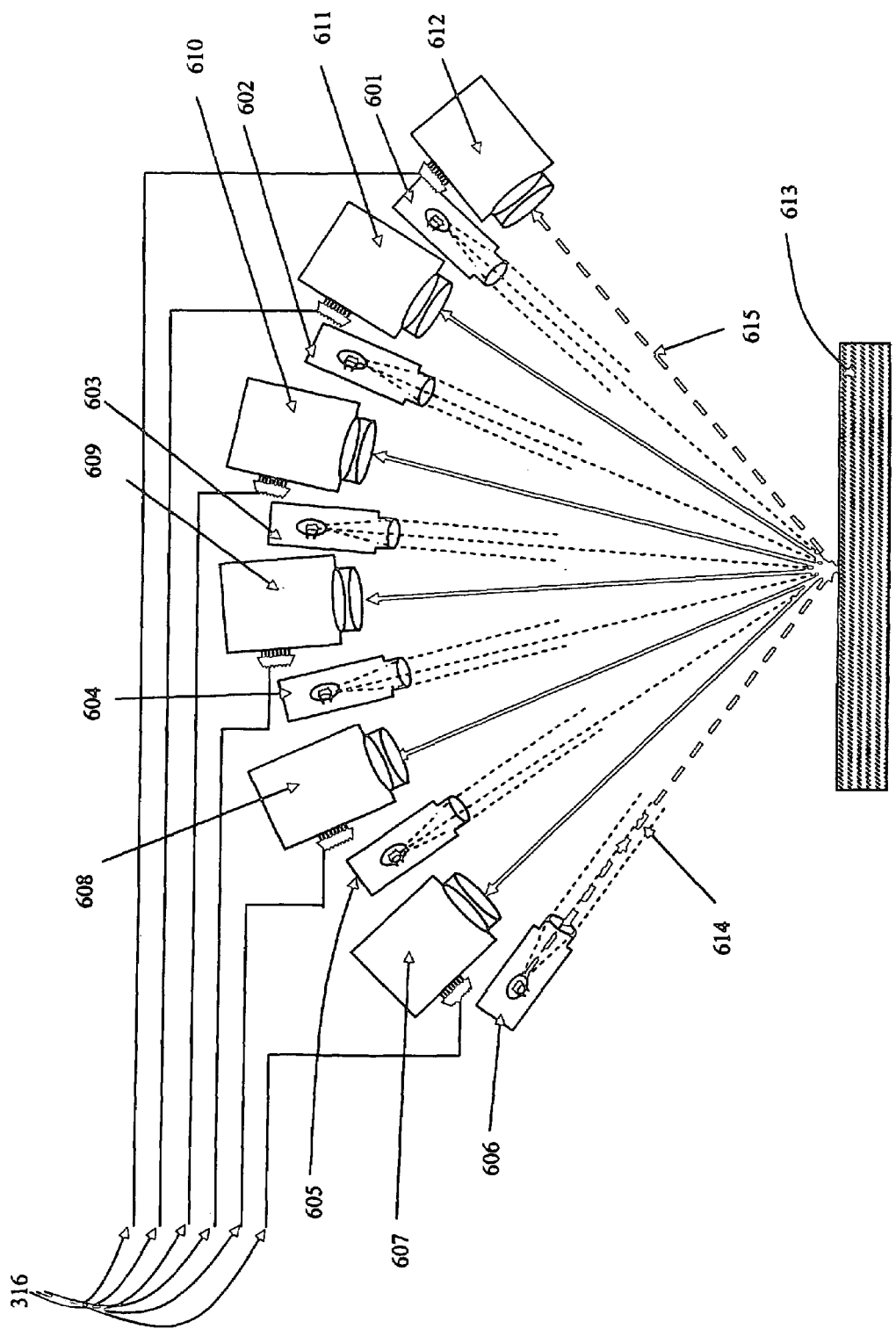
FIG. 6 is an optical schematic of another embodiment of the angular colorimeter of the invention utilizing a plurality of light sources and a plurality of detectors.

FIG. 6 is an optical schematic of another embodiment of the angular colorimeter of the invention utilizing a plurality of light sources and a plurality of detectors. In FIG. 6, plural light sources 601, 602, 603 and 604 provide light incident on the fixed sample 609 at selected angles of incidence. Light from these light sources travels along paths 605, 606, 607, 608, respectively, to sample 609 where light from the individual sources is specularly reflected by both the back and front surface of the sample along paths 610, 611, 612, 613 to detectors 614, 615, 616 and 607, respectively. Signal 618 sends information to a computing device for manipulation of the spectrum from each photodetector. Light sources 601 through 604 may take the form of integrating, diffusing sources as depicted at 201 (FIG. 2) or 301 (FIG. 3).

Figure 7:
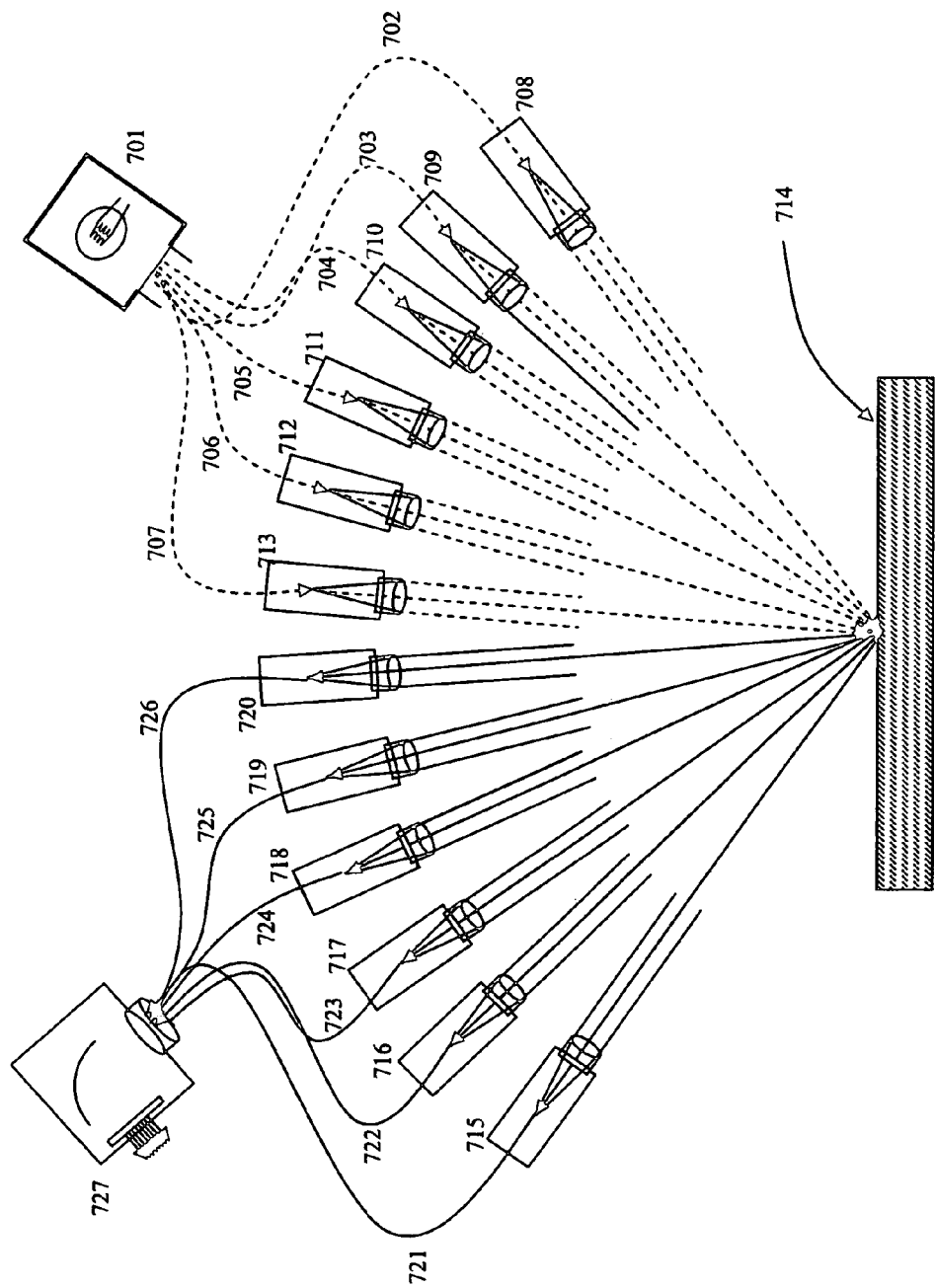
FIG. 7 is an optical schematic of another embodiment of the angular calorimeter of the invention utilizing a plurality fiber optics to couple light from a single light source to multiple positions and to couple light from multiple sets of collection optics to a single detector.

FIG. 7 is an optical schematic of another embodiment of the angular calorimeter of the invention utilizing a plurality fiber optics to couple light from a single light source to multiple positions and to couple light from multiple sets of collection optics to a single detector. In FIG. 7, light from a single light source 701 is fed by plural optical fibers (dotted lines) (702 through 707) to their respective collimating or integrating devices (708 through 713). Light sources 708 through 713 may take the form of integrating, diffusing sources as depicted at 201 (FIG. 2) or 301 (FIG. 3) in which the lamp element is replaced by a fiber optic output device.

Light from these fiber optic light sources is specularly reflected by both front and back surfaces of sample 714 along the paths indicated by solid lines. Each fiber optic light source has a set of equivalent fiber optic collection optics (one of 715 through 720) at an equal and opposite angle to the normal of sample 714 which is stationary during the measurement. The collection optics forwards the light via optical fibers (solid lines) (721 through 726) to a detector 727 which has means of sequentially selecting which particular fiber output is to be analyzed by the internal optical multi-channel analyzer.

Figure 8:
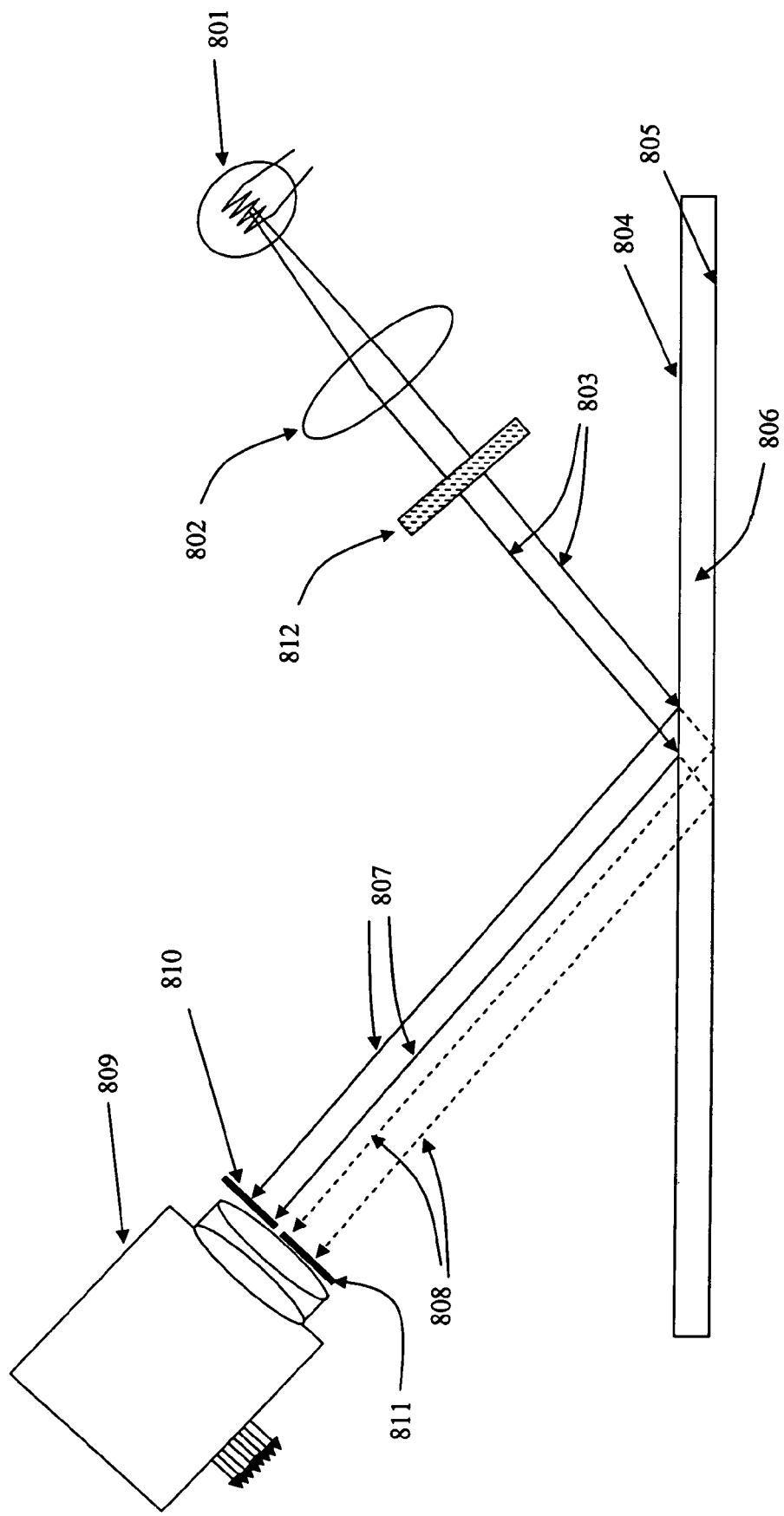
FIG. 8 is an optical ray diagram of another embodiment of the invention showing the use of shutters to selectively detect light specularly reflected from the front surface of the sample and subsequently light specularly reflected from the back surface of the sample.

FIG. 8 is an optical ray diagram of another embodiment of the invention showing the use of shutters to selectively detect light specularly reflected from the front surface of the sample and subsequently light specularly reflected from the back surface of the sample. In FIG. 8, light source 801 is collimated by optical system 802 to form a collimated beam 803 which is reflected from the front surface 804 and back surface 805 of sample 806 to form specularly reflected collimated beams 807 and 808 respectively which are directed to detector 809. Collimated beams 807 and 808 are admitted to the photodetector 809 by opening the shutters 810 and 811 sequentially to enable the separate capture of the reflection spectrum of the front and back surface. When both shutters 810 and 811 are open the combined reflectance spectrum of the front and back surface reflections from sample 806 can be measured by detector 809 as usual. In this embodiment, aperture 812 may be necessary to define the extent of the incident collimated beam and depolarizing device 813 may be used to render the incident beam randomly polarized as discussed below.

The use of shutters is applicable to other embodiments of the present invention. Shutters can be used as outlined above pertaining to FIG. 8 or may be used in front of sources or detectors or both to sequentially capture spectra.

Figure 20:
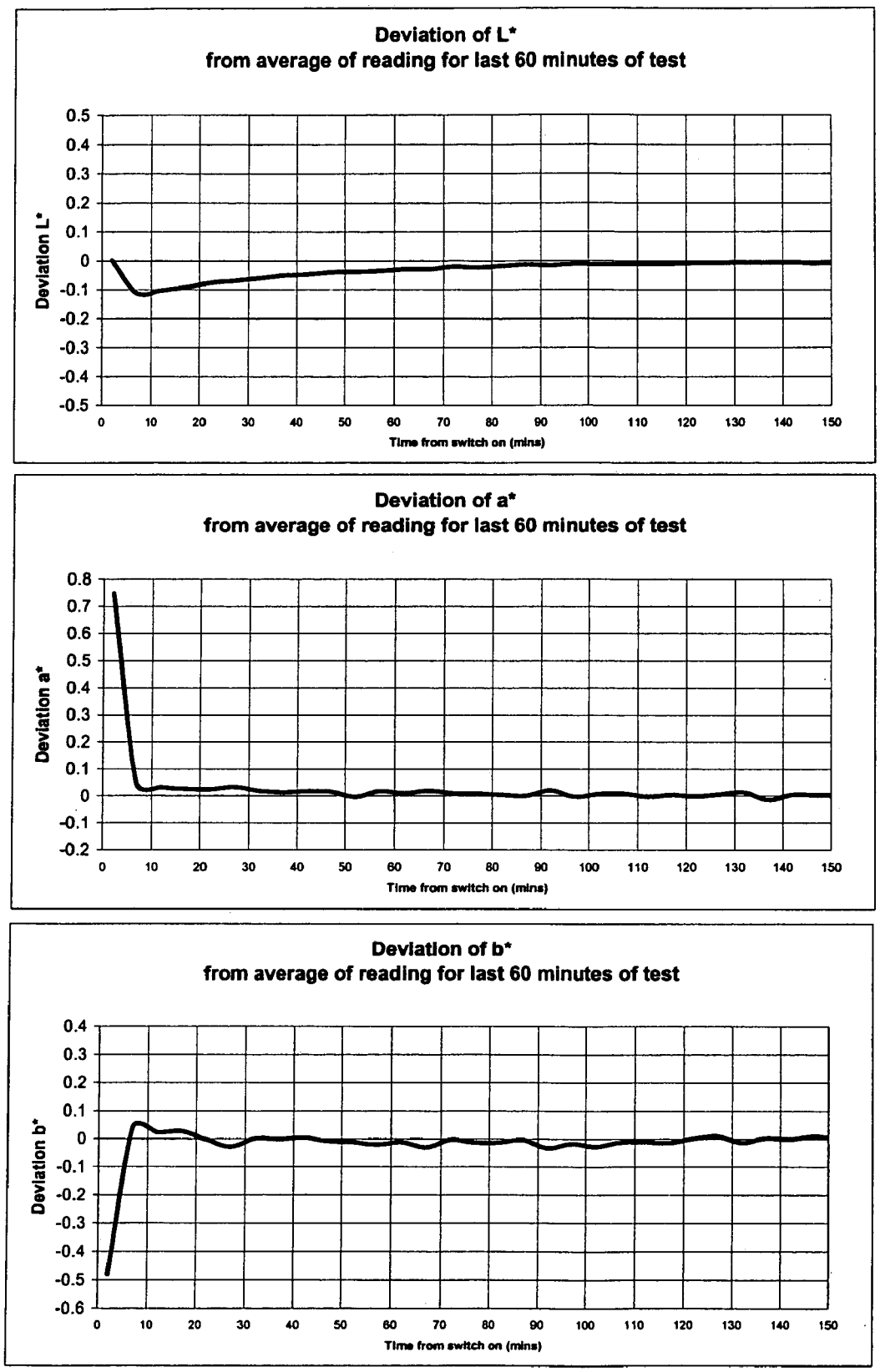
FIG. 20 is a plot of the stability of the measurements L* a* and b* as a function of time after switching on the source.

In one embodiment of the present invention, the light sources and detectors have sufficient stability over a measurement period to provide the spectral and color coordinate accuracy required. The stability of the present angular colorimeter has been measured by doing repeated measurements of the source from a few minutes after switch on to several hours. These results have shown the angular colorimeter of the present invention to be stable after the light source has been switched on for a period of 20 minutes. FIG. 20 shows the stability of the measurements L* a* and b* as a function of time after switching on the source.

The light sources of the present invention may have spectral irradiance at all wavelengths in the range 380 to 780 nm to provide accurate measurements of color coordinates according to CIE standards. For this purpose tungsten quartz lamps are suitable in many instances. The general class of lamps that are most suitable are known as quartz halogen lamps. These lamps have a tungsten filament inside a quartz envelope which contains a halogen or mixture of halogens which essentially keeps the quartz envelope from darkening due to the deposition of tungsten. One particular lamp suitable for the present invention is Product Number: W-FTD, Specialty Brand, FTD MR-11 Halogen 30° Flood Lamp, 20W, 12V with GZ4 Base, 2000 Hours Rated Life, 2900K filament temperature.

For certain purposes, it may be desirable for the light source(s) to have substantial spectral irradiance at a select number of wavelength regions in the visible, infrared (IR) or ultraviolet (UV) ranges of the electromagnetic spectrum in order to measure spectral reflectance at those regions for purpose of approximate color measurement and/or process control. Such light sources may include light emitting diodes (LEDs), gas discharge lamps, gas lasers, diode lasers, flash lamps, infrared lamps, glowbars, mercury lamps, sodium lamps among others. The photodetector(s) (e.g. item 215 of FIG. 2) may correspondingly be sensitive to any combination of wavelength regions in the IR, visible and UV.

One attribute of the invention is to ensure that the reflectance spectrum from a sample can be calibrated by firstly measuring the source directly. In the embodiment shown in FIG. 3, this calibration may be done by directly measuring the source by placing the source on the optical axis of the photodetector and removing the sample and sample holder from the optical path. In the embodiments shown in FIGS. 5, 6, 7 and 8 a front surface mirror with known spectral reflectance properties may be used in place of the sample to calibrate the source or sources.

The goniometer arrangement of FIG. 4 may be manually set to desired angles of incidence with the aid of fixed stops or may be automatically stepped to required angles of incidence by a computer control such as the above-noted stepper motor.

Figure 11:
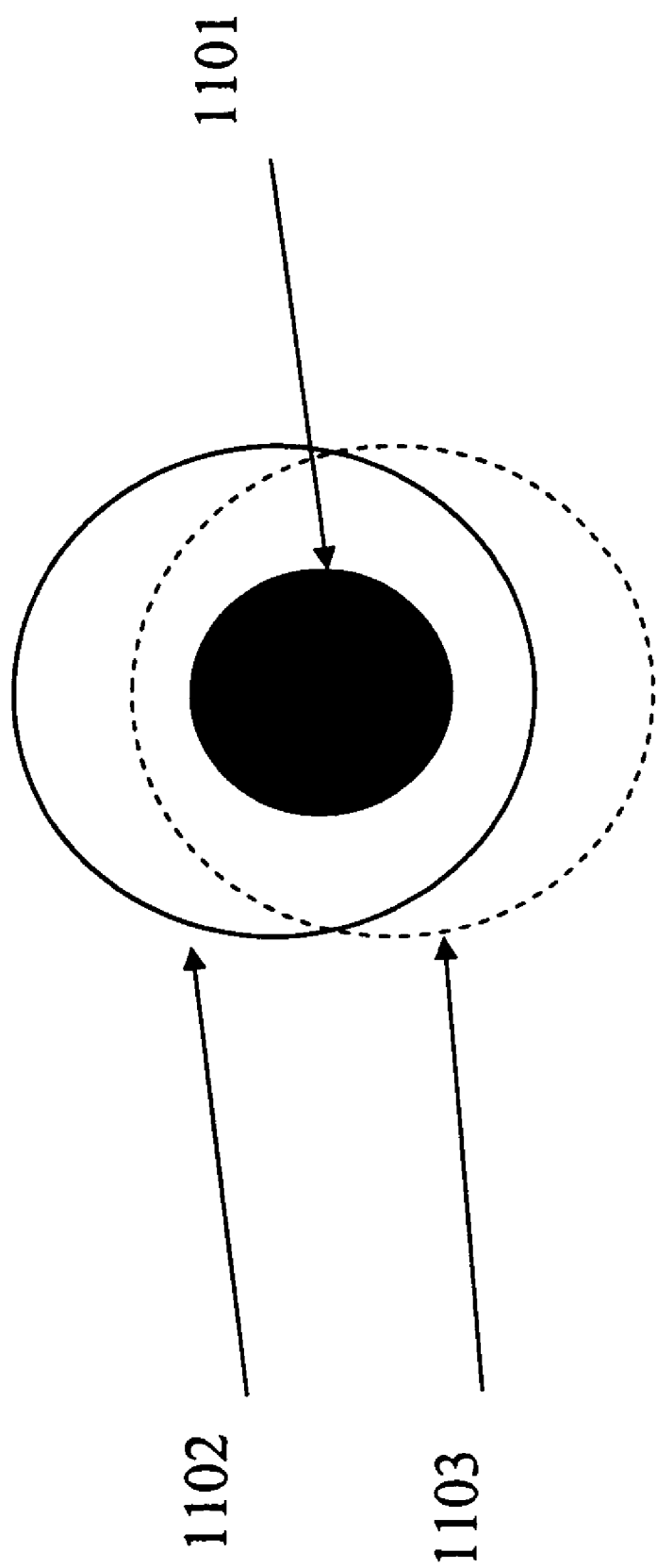
FIG. 11 is an optical schematic of respective projected images of specularly reflected light from a front side and a back side (of a thick substrate or sample) onto an image plane of a detector.

The alignment procedure checks that, at all angles of incidence, the circular graticule lies within the aforesaid overlap area thus ensuring collection of equally weighted reflectance data from both front and back surface of the sample as depicted in FIG. 11.

In one embodiment of the present invention, the influence of polarization effects is considered. Polarization of light may occur at two locations within this invention. If these polarizations are not dealt with, measurement errors may occur.

Whenever light is specularly reflected from a surface at angles other than normal incidence or grazing incidence angles, light will become partially or, in some cases, fully polarized. One source of polarization in this invention is the reflection of light off the sample being measured.

The second source of polarization occurs when the reflected beam from the sample is split into individual wavelengths for spectral or color measurement. Spreading a mixed wavelength beam into a spectrum is typically done with a diffraction grating or prism. These techniques introduce polarization. If the beam reaching the grating or prism is already partially polarized measurement errors may occur.

In one embodiment of the present invention, these polarization errors are reduced by ensuring the light is randomly polarized at two locations in the apparatus. Light from the light source must be depolarized and the beam between the sample and the grating or prism must be depolarized.

Depolarization of the light source beam may be achieved either by the use of diffusely reflected sources or by depolarizers such as that shown schematically as item 812 in FIG. 8.

Such depolarizers may consist of a rapidly rotating disk of variable optical consistency used to scramble the polarization in such a manner that the exit beam is effectively randomly polarized. Alternatively two wedges of suitable optical materials (e.g., quartz, calcite, or magnesium fluoride) may be used to form a Lyot depolarizer. A Lyot depolarizer typically includes two crystalline plane parallel plates which are cut parallel to the optic axis. The thickness ratio of the planes in the Lyot depolarizer is exactly 2:1. In a typical Lyot depolarizer, the two planes are optically contacted, the optical axes of the individual planes form a 45° degree+5 angle, and the wedge error of the combination is less than 2".

Depolarization of the light beam after it is reflected from the sample and before it reaches the grating or prism, may be accomplished by the same methods as used for the light source beam. Another common technique, which may be used for either depolarization is to pass the beam through a fiber optic light guide. The occurrence of numerous reflections of the light beam off the inner walls of the fiber randomizes the polarizations in the beam.

In certain embodiments of the present invention, sequential measurements of the reflectance spectra are performed with the incident light polarized in the p and s directions, respectively. The p polarization is that in which the electromagnetic electric vector of the incident ray is in the plane containing the normal to the sample surface and the incident ray. The s polarization is that in which the electromagnetic electric vector of the incident ray is normal to the plane containing the normal to the sample surface and the incident ray.

Polarization of the incident light may be accomplished by for example including various forms of prism polarizers (e.g. Glan Taylor prisms) and film polarizers incorporating various forms of optically aligned optical microelements including chains of molecules such as in polymer films. Two such polymer polarizers are available under the trade name POLAROID™.

Figure 9:
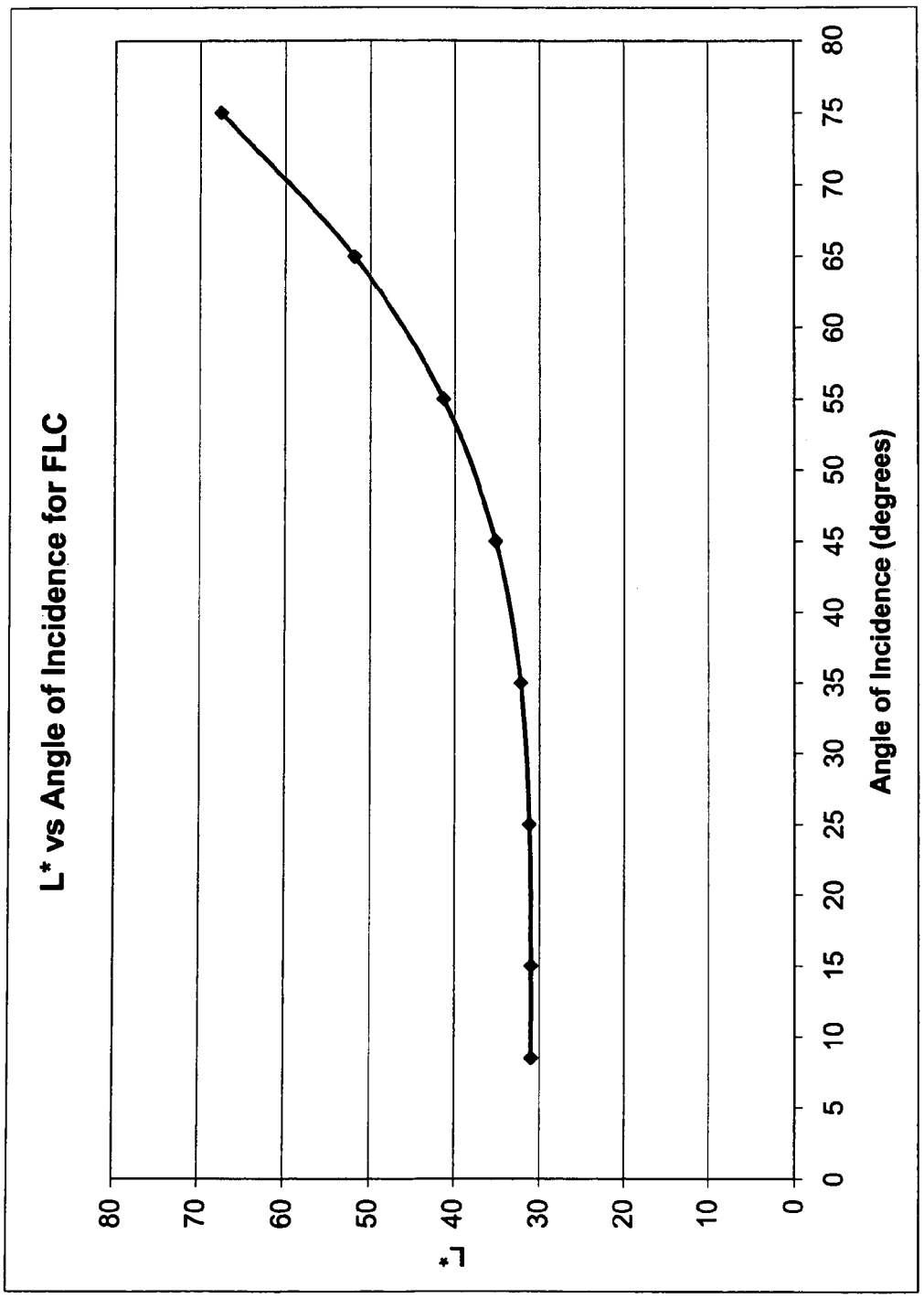
FIG. 9 is a plot of detected light received from the sample as a function of angle measure by the angular colorimeter of the present invention and displayed according to a color coordinate.

FIG. 9 is a plot of detected light received from the sample as a function of angle measure by the angular calorimeter of the present invention and displayed according to a color coordinate. More specifically, FIG. 9 shows an example result of a measurement of a coated glass surface wherein the Lab parameter L* is plotted against the angle the angle of incidence. The present angular colorimeter has been compared at 8.5 degrees to results from a BYK™ Gardner instrument based on an integrating sphere and found in reasonable agreement over the range of color values representing "in spec" coatings.

Figure 10:
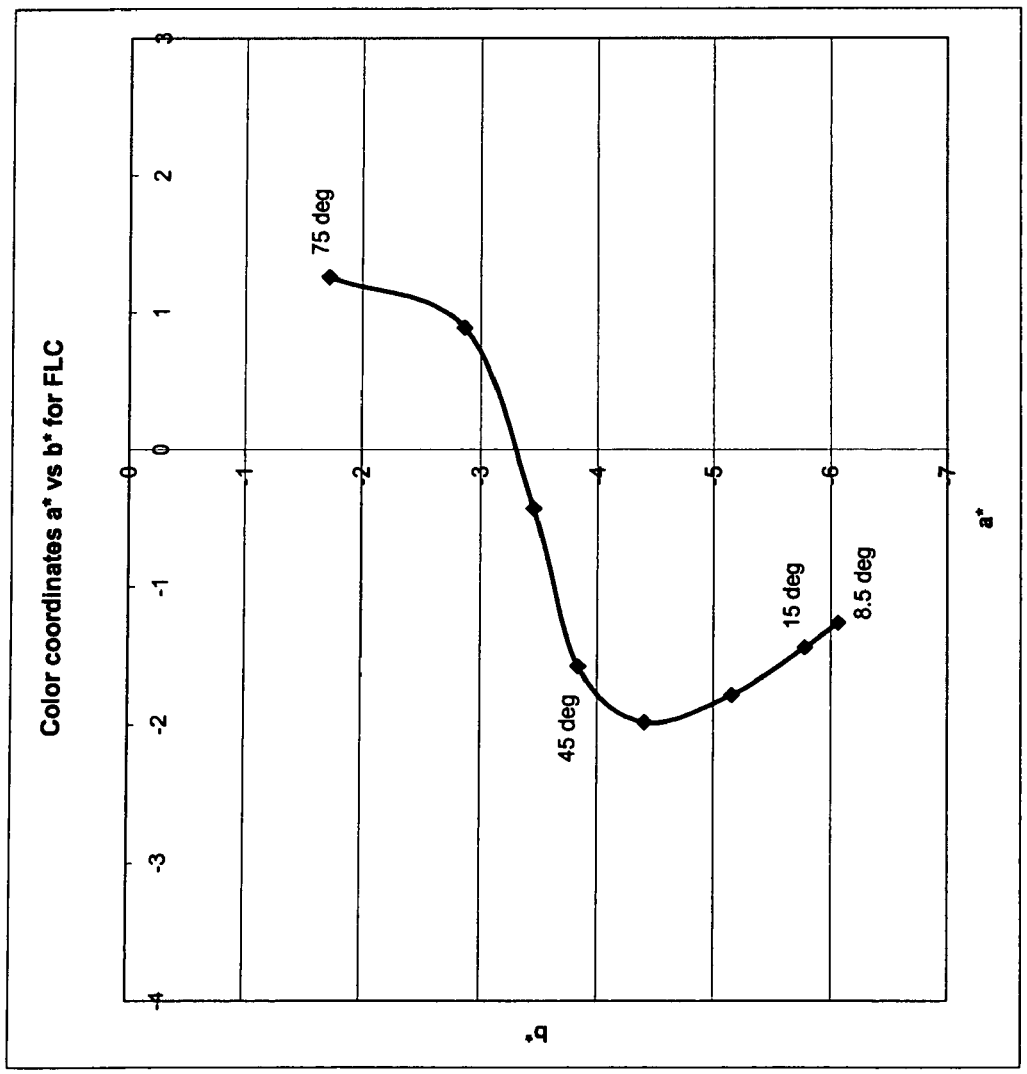
FIG. 10 is a plot of detected light received from the coated side of the sample as a function of color coordinates.

FIG. 10 is a plot of detected light received from the coated side of the sample as a function of color coordinates. More specifically, FIG. 10 shows an example result of a measurement of a coated glass surface wherein the Lab parameters a* and b* are plotted against each other as the angle of incidence varies from 8.5 degrees through 15, 25, 35, 45, 55, 65 and 75 degrees. The parameters a* and b* are consistent with that established by the Commission Internationale de l'Eclairage and discussed in U.S. Pat. No. 6,985,254; the entire contents of which are incorporated herein by reference. In this system, CIE L*a*b* space, is a tristimulus color space with the coordinates L*, a*, and b*. The central vertical axis (L*) represents lightness, with values from 0 (black) to 100 (white). The two color axes each run from positive to negative. On the a-a' axis (a*), positive values indicate amounts of red while negative values indicate amounts of green. On the b-b' axis (b*), yellow is positive, and blue is negative. For both the a-a' axis and the b-b' axis, zero is neutral gray. A single specific color can be uniquely identified with a value for each color axis, and a value for the lightness or grayscale axis. CIE L*a*b* space is device-independent. In practice, this system uses the following numerical calculations $$X = k \int_{380\ nm}^{780\ nm} S(\lambda) R(\lambda) \bar{x}(\lambda)\, d\lambda$$

$$Y = k \int_{380\ nm}^{780\ nm} S(\lambda) R(\lambda) \bar{y}(\lambda)\, d\lambda$$

$$Z = k \int_{380\ nm}^{780\ nm} S(\lambda) R(\lambda) \bar{z}(\lambda)\, d\lambda$$

$$\text{for } k = \frac{100}{\int_{380\ nm}^{780\ nm} S(\lambda) y(\lambda)}$$

where $S(\lambda)$ is the spectral distribution of illumination, $R(\lambda)$ is the spectral reflectance of object, and $\bar{x}(\lambda), \bar{y}(\lambda), \bar{z}(\lambda)$:

are color matching functions.

The CIELAB colorimetric system is defined by:

$$L^* = 116 f\left(\frac{Y}{Y_n}\right) - 16$$

$$a^* = 500\left\{ f\left(\frac{X}{X_n}\right) - f\left(\frac{Y}{Y_n}\right) \right\}$$

$$b^* = 200\left\{ f\left(\frac{Y}{Y_n}\right) - f\left(\frac{Z}{Z_n}\right) \right\}$$

$$f\left(\frac{X}{X_n}\right) = \begin{cases} \left(\frac{X}{X_n}\right)^{\frac{1}{3}}, & \frac{X}{X_n} > 0.008856 \\ 7.787\left(\frac{X}{X_n}\right) + \frac{16}{116}, & \frac{X}{X_n} \leq 0.008856 \end{cases}$$

f(Y/Yn) and f(Z/Zn) are similarly calculated.

FIG. 11 is an optical schematic of respective projected images of specularly reflected light from a front coated side and a back side onto an image plane of a detector. More specifically, FIG. 11 shows a representation of the view seen through the PR650 SPECTRASCAN™ photodetector device wherein the black filled circle 1101 represents the circular graticule of the SPECTRASCAN™ unit and coincides with the light collection area of the photodetector. The solid and dotted circles represent the overlap of the two images 1102 and 1103 from the front and back surfaces of the coated glass sample, respectively.

Figure 12:
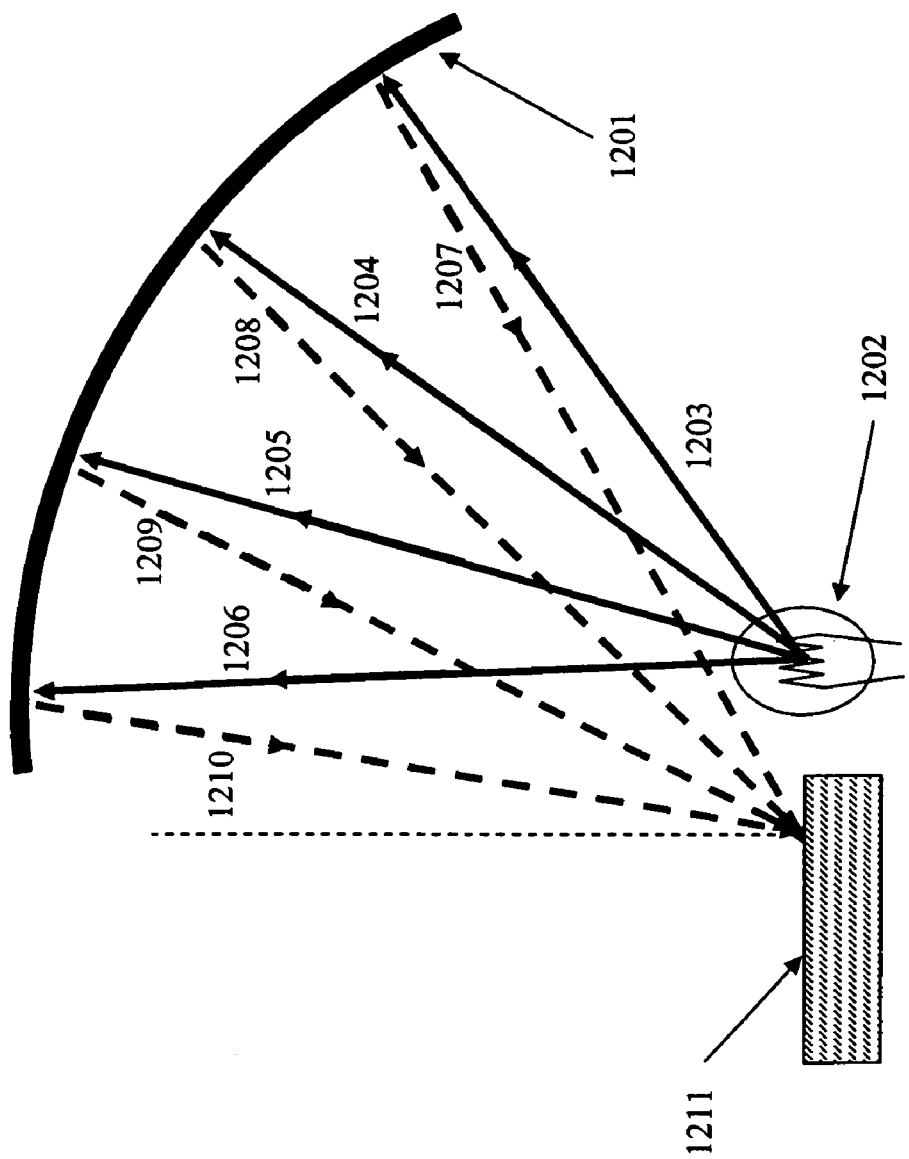
FIG. 12 is an optical schematic of another embodiment of the angular colorimeter of the invention utilizing a single light source and a section of a hemispherical diffuse reflector to project light onto a sample.

FIG. 12 is an optical schematic of another embodiment of the angular colorimeter of the invention utilizing a single light source and a section of a hemispherical mirror or diffuse reflector to project light onto a sample. In FIG. 12, an extended light source is shown similar to item 501 in FIG. 5. In FIG. 12, the extended source 1201 is either a curved mirror or a curved diffuse white reflector. In either case the light from light source 1202 travels along paths 1203, 1204, 1205, 1206 and returns from curved device 1201 along paths 1207, 1208, 1209, 1210 to the sample 1211 as required. The light source 1202 can be of many different types including a tungsten lamp, a tungsten halogen lamp, a miniarc lamp or a flash lamp. The light source 1202 and the sample 1211 are represented as being in planes slightly in and out of the plane of the diagram so that the light source 1202 and the sample 1211 do not have to occupy the same physical space for the optical arrangement to function correctly. FIG. 12 is a slightly oblique view of the physical arrangement.

Figure 13:
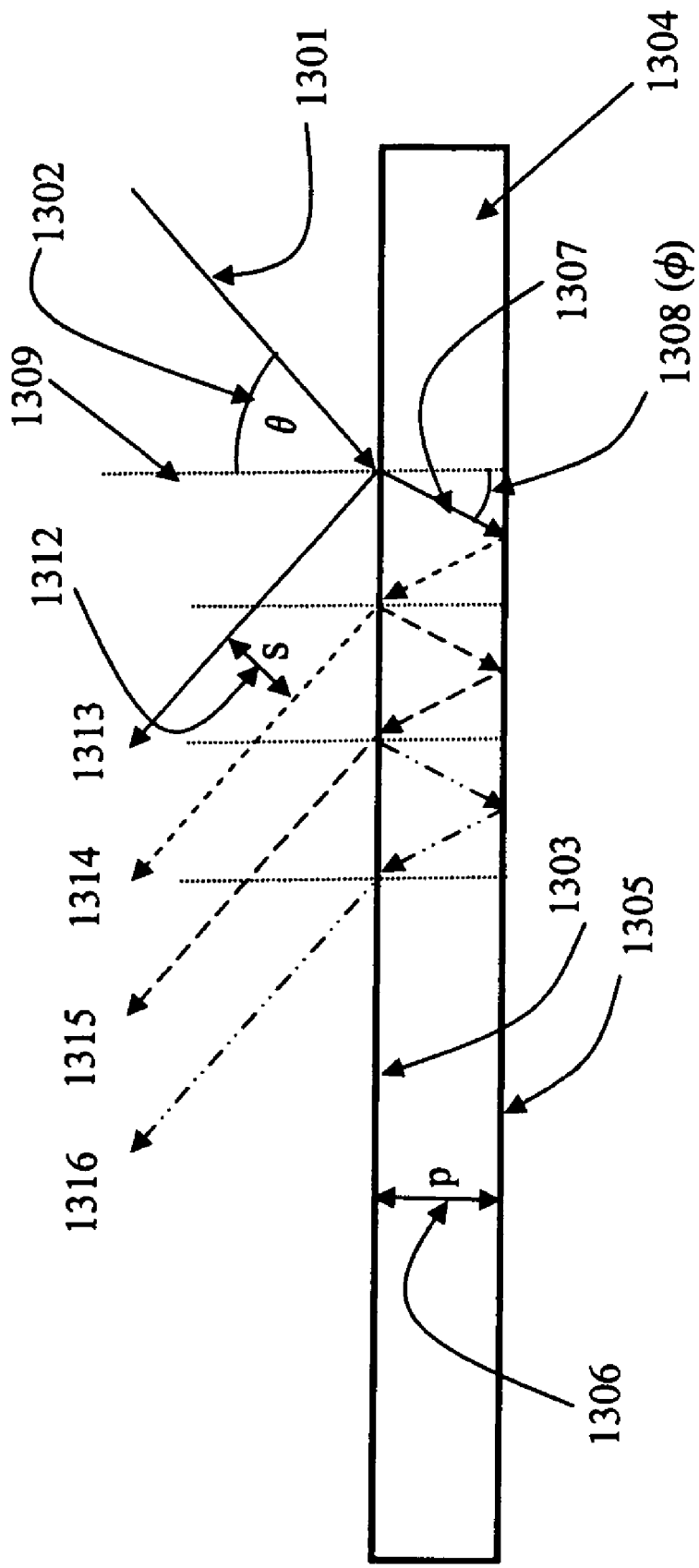
FIG. 13 is an optical ray diagram according to one embodiment of the angular colorimeter of the present invention that depicts multiple internal specular reflections from a sample plate.

FIG. 13 is an optical ray diagram according to one embodiment of the angular colorimeter of the present invention that depicts multiple internal specular reflections from a sample plate. More specifically, FIG. 13 illustrates the multiple internal reflections due to a single incoming light ray 1301 of intensity "I" incident at an angle θ (1302) to the front surface 1303 of an object 1304 which has a back surface 1305 and thickness "p" (1306). The first transmitted ray 1307 is refracted at an angle φ (1308) to the surface normal 1309. The primary reflected ray is 1313 which we will designate $R_1$. Internal reflections give rise to several secondary reflected rays 1314, 1315, 1316, etc. of ever decreasing magnitude as shown in the FIG. 13. These reflections are designated here for the purposes of illustration as $R_2$, $R_3$ and $R_4$ respectively. Further, the external first surface reflectance is designated as $R_e$, the external or internal first surface transmittance of the incident ray is designated as T, the internal reflectance of the front surface is designated as $R_f$, the internal reflectance of the back surface is designated as $R_b$, the internal transmittance of the substrate is designated as $T_s$. Accordingly, $R_1 = I\,R_e$ $$R_2 = IT^2 R_b (T_s)^2$$

$$R_3 = IT^2 (R_b)^2 (R_f)(T_s)^4$$

$$R_4 = IT^2 (R_b)^3 (R_f)^2 (T_s)^6$$

Assuming I=1 and reasonable values of $$R_e = 4\%, T = 96\%, R_b = 20\%, R_f = 4\% \text{ and } T_s = 99.6\%,$$

$$R_1 = 1*0.04 = 0.04 = 4\%$$

$$R_2 = 1*(0.96)^2 * 0.20*(0.996)^2 = 0.183 = 18.3\%$$

$$R_3 = 1*(0.96)^2*(0.20)^2*(0.04)* \\ (0.996)^4 = 0.00145 = 0.145\%$$

$$R_4 = 1*(0.96)^2*(0.20)^3*(0.04)^2* \\ (0.996)^6 = 0.0000115 = 0.0012\%$$

Thus, the third reflection $R_3$ therefore has an intensity which is 0.65% of the incoherent combination of the first two reflections $R_1$ and $R_2$. For typical architectural glass industry energy efficient coatings, the error in color coordinates is no more than 0.1 and is therefore negligible for all practical purposes.

Thus, the fourth reflection $R_4$ therefore has an intensity which is of 0.005% of the incoherent combination of the first three reflections $R_1$, $R_2$ and $R_3$ and is therefore entirely negligible for practical purposes.

FIG. 13 is also illustrative of one aspect of the present invention. This aspect is that, if the source is a collimated beam of diameter "w", the receiving optics must have an aperture large enough to capture both the first reflected ray 1313 and the second reflected ray 1314 which is a result of ray 1307 undergoing one back surface internal reflection.

To calculate the separation "s" (1312) between these first and second reflections 1313 and 1314, let:

"a" be the length of ray 1307 inside the object

"n" be the refractive index of the object

"p" (1306) be the thickness of the object

"θ" (1302) be the angle of incidence

"φ" (1308) be the angle of refraction

Then:

$$n = \sin\theta / \sin\phi$$

so $$\phi = \sin^{-1}((\sin\theta)/n)$$

from which $$s = 2a \tan\phi \cos\theta$$

For example, if n=1.53 for soda glass and the thickness "p" of the glass object is 15 mm, the perpendicular separation distance "s" between the first and second reflection has a maximum value of 11.15 mm at an angle of incidence of 50 degrees. Thus, the collection aperture for a detector should have one dimension at least equal to the separation distance "s" plus the beam width "w"(item 108 of FIG. 1) in the plane of incidence which includes the incident ray and the normal to the object front surface.

The minimum width of the beam is determined by the collection efficiency of the photodetector, its noise properties, and the irradiance of the source. One embodiment of the invention utilizes a 20 watt tungsten halogen lamp (such as described above) and a beam width of 7 mm. Thus, the collection aperture would for this example have at least one dimension greater than 18 mm to collect both first and second reflected rays 1313 and 1314, respectively, and their corresponding beams of width "w". In fact, the collection aperture should be considerably larger than 18 mm (e.g. about 25 mm) to allow for minor misalignments within the apparatus and the mounting of the sample in the sample holder. Furthermore, the collection optics are preferably uniform in their efficiency across the entire aperture to avoid introduction of unacceptable errors in the measurement of optical properties such as total reflectance and color coordinates. The uniformity of the present angular colorimeter of the present invention has been checked in a self-consistent manner and shown to be uniform for the illumination source area utilized.

To avoid relatively large, sophisticated optics, one embodiment of the invention as illustrated in FIG. 2, may be considered to be the reverse optical path of FIG. 13. In FIG. 13, imagine that, using the principle of reversibility in optics, all the paths have their arrows reversed so that 1301 is now an output ray to a photodetector and rays 1313, 1314, 1315 etc. are input rays from an extended source which is considerably easier to manufacture than a large uniform detector.

Figure 14:
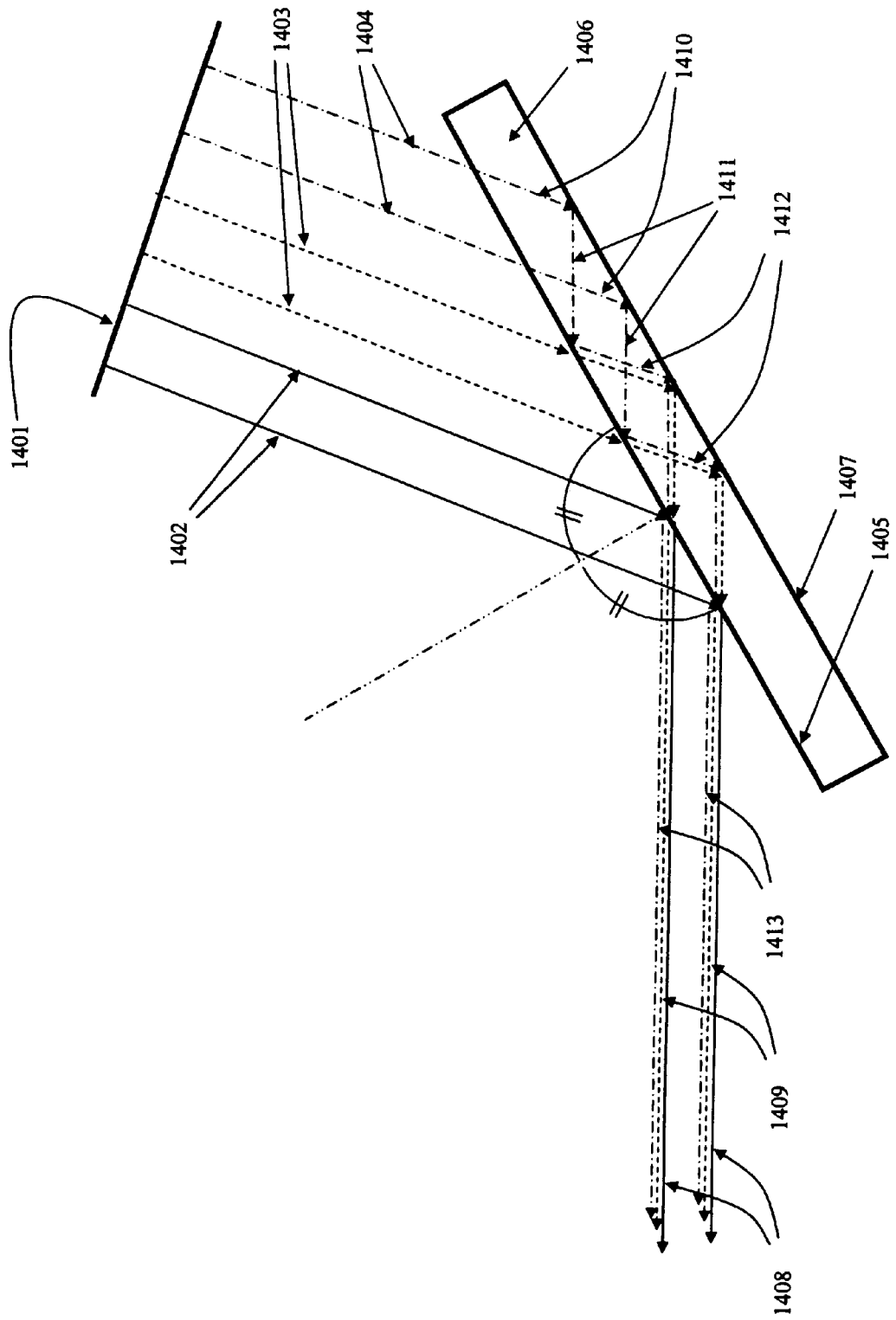
FIG. 14 is an optical ray diagram according to one embodiment of the angular colorimeter of the present invention that depicts multiple internal specular reflections from a sample plate and shows those of which pass to a detector.

FIG. 14 is an optical ray diagram according to one embodiment of the angular colorimeter of the present invention that depicts multiple internal specular reflections from a sample plate and shows those of which pass to a detector (as referred to immediately above). Here, in this illustration, an extended source 1401 provides light along paths 1402, 1403, 1404 which are incident at equal angles to the front surface 1405 of object 1406 which has a back surface 1407. The rays 1402 are reflected at the front surface 1405 along paths 1408 towards the detector (not shown).

Rays 1403 suffer one back surface reflection and travel along paths 1409 to the photodetector. Rays 1404 suffer one back surface and one front surface internal reflection as they travel along paths 1410, 1411, 1412 and 1413 to the detector. A source with one dimension at least "s"+"w" feeds an aperture of dimension "w" where all dimensions are measured in the plane of incidence and reflection.

Thus, for a detector of acceptance aperture dimension "w"=7 mm, the present invention in one embodiment utilizes a uniform source of dimension s+w=18 mm for a glass object of thickness 15 mm at an angle of incidence of 50 degrees.

The source 202 acts as an integrating sphere producing uniformity over the viewing area of 1401 as depicted at 202 in FIG. 2 wherein 1401 replaces element 203. In order to cope with misalignments of say +/−3.5 mm, the present invention in one embodiment utilizes a uniform source of dimension 25 mm. These considerations are in effect especially for the embodiments represented by FIGS. 5, 6, and 7, where fixed detectors at a plurality of positions are envisaged.

Figure 15:
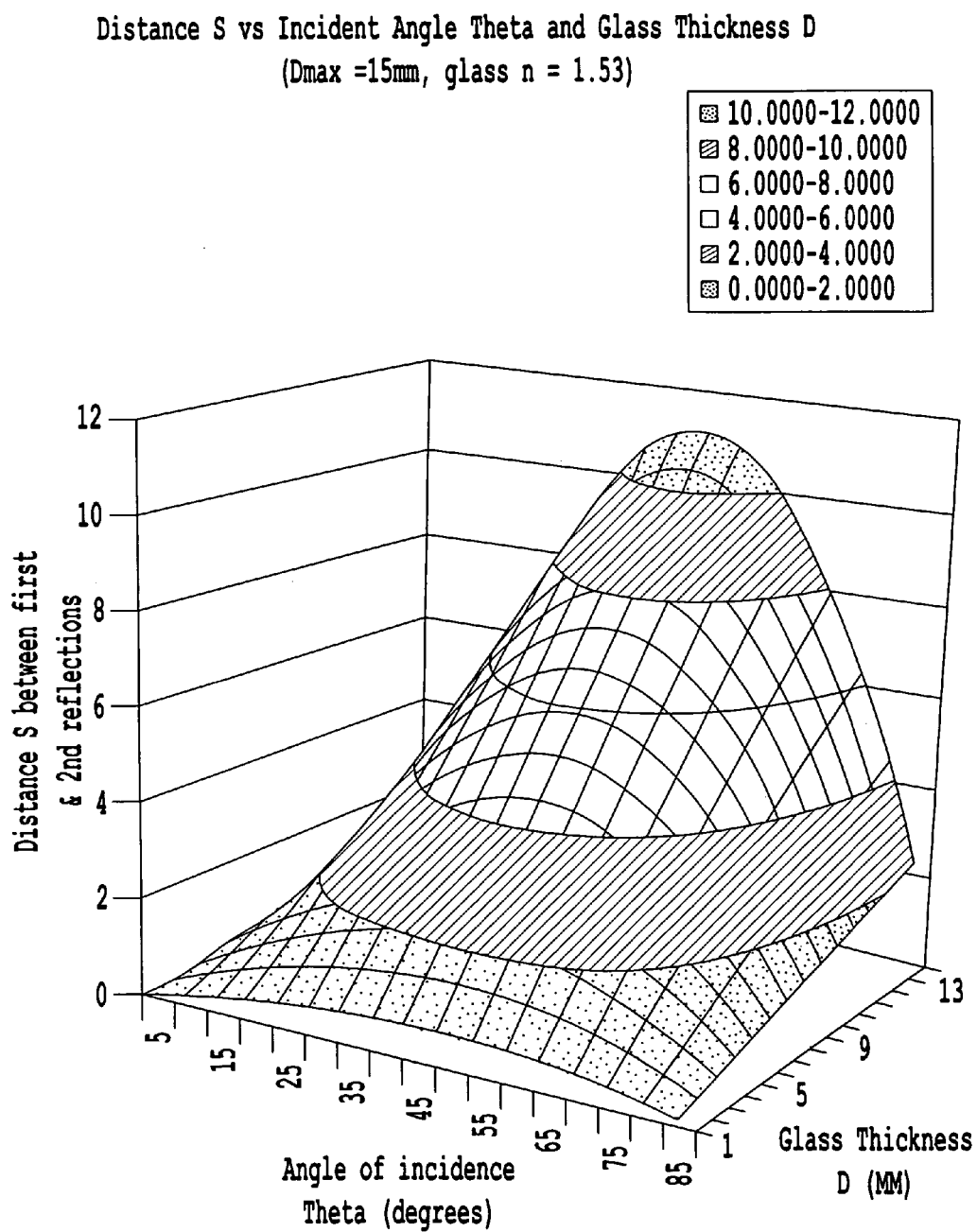
FIG. 15 is a plot of the dependence of separation distance between a first and second specularly reflected light beam on the sample thickness and on the angle of incidence of the reflected light.

FIG. 15 is a plot of the dependence of separation distance s between a first and second specularly reflected light beams on sample thickness (p) and on angle of incidence of the incident and reflected light. More specifically, FIG. 15 shows a plot of the separation distance "s" as a function of angle of incidence and glass thickness for a glass object of refractive index 1.53. The plot will change with the refractive index of the glass. The maximum separation distance "s" can be determined from the data presented in FIG. 15 for any sample thickness. This allows the design of the source so that its uniform dimension in the plane of incidence complies with the requirement that it be larger than "s"+"w" as discussed beforehand.

Figure 16:
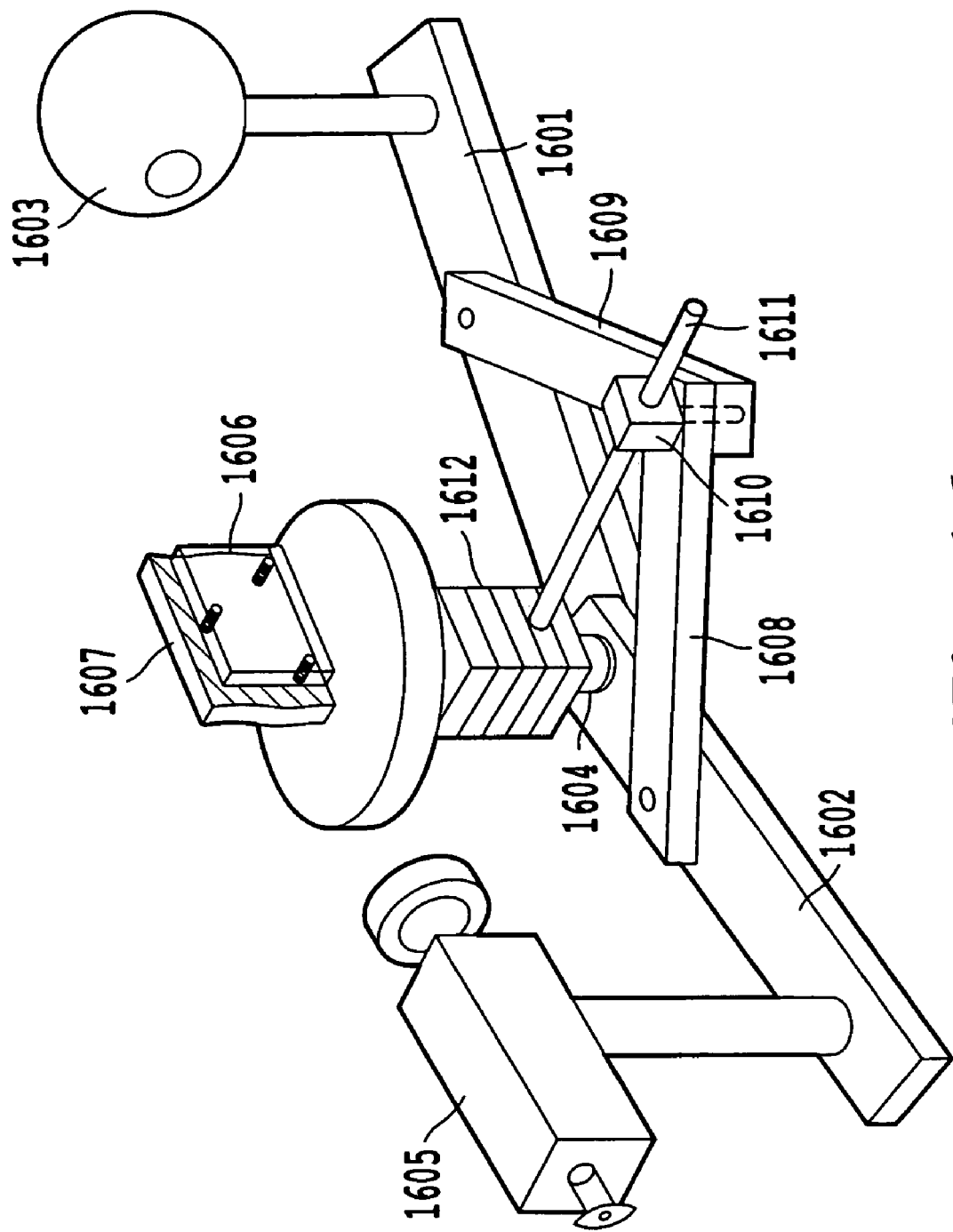
FIG. 16 is an optical schematic of another embodiment of the angular calorimeter of the invention utilizing a pantographic arm configured for simultaneous angular movement of a single source and detector.

FIG. 16 is an optical schematic of another embodiment of the angular colorimeter of the invention utilizing a pantographic arm configured for simultaneous angular movement of a single source and detector. More specifically, FIG. 16 shows an alternative means of accomplishing the required simultaneous angular movement of a single source and detector such that the detector always gathers the specularly reflected light from a sample as the angle of incidence of the light on the sample is varied.

As shown in FIG. 16, the pantograph includes a fixed arm 1601 and movable arm 1602. The fixed arm is fastened to a bench and supports a light source 1603 at one end. The source is a uniform spot such as is produced by a multi-reflectant spherical cavity. The other end of the fixed arm supports a vertical bearing rod 1604. The movable arm is free to rotate about this vertical bearing rod. The other end of the movable arm 1602 supports a detector 1605 which is directed at the surface of the sample 1606. A sample holder 1607 is mounted on the vertical bearing rod and is free to rotate.

Two pantograph arms 1608 and 1609 are connected to bearings on the arms and also to each other at a bearing connected to the pivot block 1610. An angle guide rod 1611 runs through the pivot block and is anchored into the sample holder support 1612. This rod controls the orientation of the sample holder. When the movable arm 1602 is rotated about the vertical bearing 1604, the pantograph arrangement causes the angular displacement of the sample holder 1607 to be exactly half as much as the movable arm. The reflected image of the source is thus always visible through the detector telescope 1605 as the reflectance angle is varied.

In operation of the pantograph device, the arms are set to 180 degrees apart and the sample is removed from the path between the detector and the source. This configuration is used to align the instrument optically. The detector is adjusted to be in line with the vertical bearing rod and level horizontally. The source is adjusted to be centered in the detector field of view. The source is measured to establish the 100% reflectance value.

With the sample in place and the movable arm at values between 160 degrees and 15 degrees, the sample is adjusted so that the front reflecting surface is aligned with the center of rotation of the vertical bearing rod, and the reflected view of the source is visible in the center of the photodetector field of view. The sample can now be measured for reflectance at any angle between about 160 and about 15 degrees, (included angle). The angle of incidence is half the included angle for all values of included angle.

Besides architectural glass evaluation, the present angular calorimeter has application in other fields such as for example in the analysis of color shifting pigments, patterned glass (shower doors, privacy glass etc.), anti reflective coatings, textured surfaces, diffuse (as opposed to specular) surfaces, and active films (such as electrochromic, photochromic or SPD (suspended particle device), paint, enamel, glazes, tapes, films, printed articles, metals, ceramics, liquids, cloth, hair, building materials, skin, food, etc.

Although a number of the foregoing examples may involve a significant amount of diffuse reflectance (so that the measured reflectance will be a mixture of specular and diffuse reflectance), the present angular colorimeter is nonetheless useful in situations where either of the reflectances or their ratio is known or known to be constant.

Figure 17:
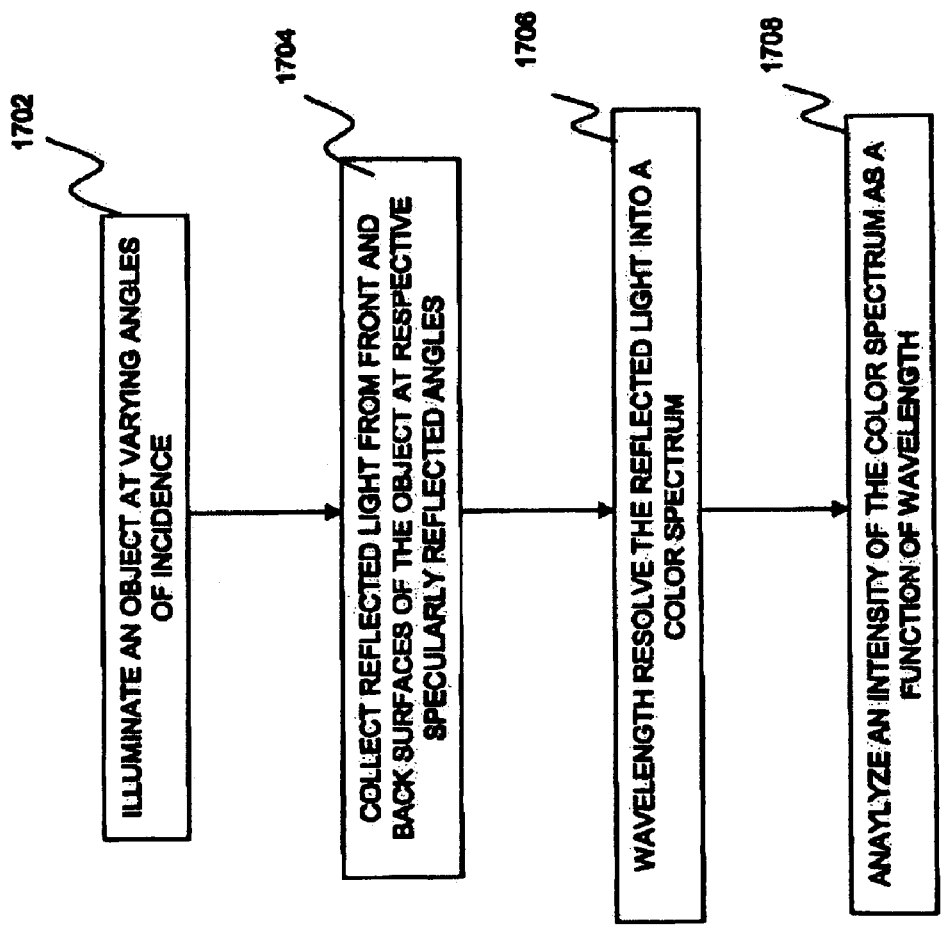
FIG. 17 is a flowchart depicting one method according to the present invention.

Accordingly, as illustrated in the numerous examples above, the present invention provides a method for measuring the reflectance properties of an object having a front reflecting surface and at least one back reflecting surfaces. FIG. 17 is a flowchart depicting a general method according to the present invention. At 1702, an object is illuminated at varying angles of incidence. At 1704, reflected light from the front and back reflecting surfaces of the object is collected (for example by detector optics focusing the reflected light) at respective specularly reflected angles. At 1706, the reflected light is wavelength resolved into a color spectrum. At 1708, an intensity of the color spectrum as a function of wavelength is analyzed.

At 1702, the object can be illuminated from a diffuse reflecting surface light source such as for example the light source 202 in FIG. 2 or the light source 1603 in FIG. 16. As noted above, in one embodiment of the present invention, a tungsten halogen lamp can be used with a barium sulphate diffuser. At 1702, the illumination can be from an extended angular light source that emits light onto the object over a range of incident angles (e.g. at least 45 degrees from normal to the object or preferably up to at least 75 degrees).

Further, the illumination from the light source can be passed through a diffusing device that diffuses (and randomly polarizes) light from the light source, or through a depolarizing device that randomly polarizes light from the light source, or through both. Further, polarizers can be placed on an optical path between the source and the detector to allow the separate measurement of the total specular reflectance of the front and back reflecting surfaces of an object in both a plane of polarization in the plane of incidence and a plane of polarization normal to the plane of incidence. Moreover, the illumination can be from an extended light source configured to provide an extended curved optically diffuse source or a specularly reflecting or diffuse reflecting device from a single lamp.

At 1704, the specular reflections from the object can be directed to a detector, which remains in a fixed position, as an angular position of the object relative to the detector or the light source is varied. For example, the goniometer device depicted in FIG. 4 can be used with sample stage and light source rotating on arms 401 and 406, or the pantographic device depicted in FIG. 16 can be used in which arm 1602 remains stationary. At 1704, the detector can remain fixed while the light source moves at twice the angular rate as the object. Alternatively, the light source can remain fixed while the detector moves at twice the angular rate as the object. For example, the goniometer device depicted in FIG. 4 can be used with sample stage and detector rotating on arms 401 and 406, or the pantographic device depicted in FIG. 16 can be used in which arm 1601 remains stationary. At 1704, the light collected can be from a front reflecting surface and a back reflecting surface of the object that are separated by a distance of at least one millimeter.

Furthermore, at 1704, shutters can be used to permit separate measurement of the specular reflectance of the back and front surface reflections of the object. Furthermore, the collected light can be from an insulated glass unit (IGU) or mockup thereof or from articles described above (i.e., color shifting pigments, patterned glass, anti reflective coatings, textured surfaces, diffuse surfaces, and active films, paint, enamel, glazes, tapes, films, printed articles, metals, ceramics, liquids, cloth, hair, building materials, skin, food, etc.

At 1706, the wavelength resolution can occur using a spectral photodetector. Furthermore, the analysis at 1708 can provide a spectral measurement of the reflected light from the object.

At 1708, the analysis can be based on signals from a plurality of detectors arranged at a plurality of angles to the object. For example, the light source can be a plurality of light sources arranged at a plurality of angles to the object (See for example FIGS. 6 and 7). Furthermore, at 1708, in one embodiment of the present invention, signals from an output device of for example a detector are provided that are indicative of color intensities of the reflected light.

Color intensities can be used to classify the reflected light for example using the CIE chromaticity diagram. The CIE system characterizes colors by a luminance parameter Y and two color coordinates x and y (or a* and b*) which specify the point on the chromaticity diagram. The CIE system uses parameters that are based on the spectral power distribution (SPD) of the light and that are factored by sensitivity curves which have been measured for the human eye. According to the CIE standard and based on the fact that the human eye has three different types of color sensitive cones, the response of the eye is best described in terms of three "tristimulus values". However, once this is accomplished, it is found that any color can be expressed in terms of the two color coordinates x and y. The colors which can be matched by combining a given set of three primary colors (such as the blue, green, and red) are represented on the chromaticity diagram by a triangle joining the coordinates for the three colors.

Figure 21:
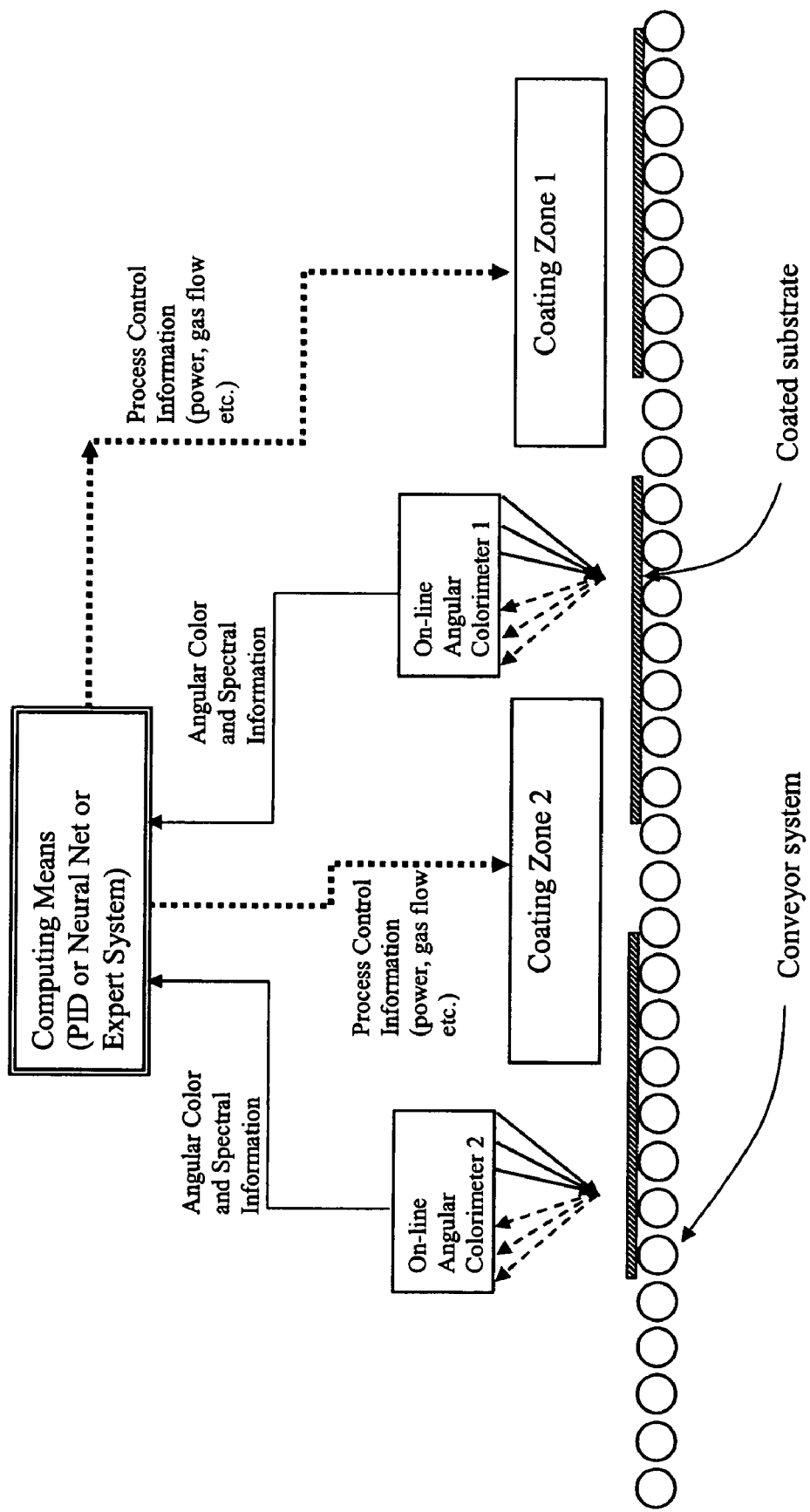
FIG. 21 is a schematic of an on-line control system according to one embodiment of the present invention.

Thus, quantifications such as shown in FIG. 10 are made in one embodiment of the present invention to remove a subjective measure of the visible color of an object. Furthermore, as detailed above, angular color data gathered can be used by process control configured to control a coating process in real time. Accordingly, process control of a glass (or other object manufacturing process) can include artificial intelligence operating on the angular color data. FIG. 21 is a schematic of an on-line control system according to one embodiment of the present invention. As shown in FIG. 21, two (although more could used) angular colorimeters of the present invention are used at various stages (e.g., coating zones 1 and 2) of a manufacturing glass facility. In one embodiment of the present invention, only one angular colorimeter could be used for process control in a feedback loop to a single coating station such that future coatings are adjusted based on the result of the present coating. A computing device controls the stages and accepts data from the angular calorimeters in order to adjust the coating conditions (as discussed earlier). Such a process not only provides control but removes subjective determinations as to whether the coating conditions are to standard.

Further, in one aspect of the present invention (used for example for calibration), the object can be removed from an optical path from the detector to the light source such that a reference spectrum of the white light can be measured. Accordingly, at 1708, a computing device can be used to ratio a signal corresponding to the reflected signal from the object to a reference signal corresponding to direct light from the source to provide a radiometric total specular reflectance of the object. Furthermore, at 1708, data from the detector can be used by a computing device to produce (from the angular positions and from wavelength resolution of the reflected light) angular color data. In one embodiment of the present invention, the computing device can provide the angular color data to for example a process controller for control of glass manufacturing or glass coating process. As noted above, the process controller can include artificial intelligence algorithms operating on the angular color data to provide instructions to the glass manufacturing or glass coating process.

Numerous modifications and variations on the present invention are possible in light of the above teachings. It is, therefore, to be understood that within the scope of the accompanying claims, the invention may be practiced otherwise than as specifically described herein.

The invention claimed is:

1. An apparatus for measuring reflectance properties of an object having a front reflecting surface and a back reflecting surface, comprising:
   a sample stage for placement of the object;
   a light source;
   a detector configured to detect reflected light from the object; and
   a positioning device configured to provide a plurality of angular positions for the light source and the detector relative to the object on the sample stage such that incident light on the object is specularly reflected towards the detector and the reflected light received at the detector includes a front surface reflection from the object and at least one back surface reflection from the object.

2. The apparatus of claim 1, further comprising an output device configured to provide signals from the detector indicative of spectral intensities of the reflected light.

3. The apparatus of claim 1, wherein the positioning device comprises:
   a goniometer configured to position the sample stage, the detector, and the light source relative to one another such that specular reflections from the object directed to the detector remain at a fixed angle to the detector as an angular position of the object relative to at least one of the detector and the light source is varied.

4. The apparatus of claim 1, wherein the light source comprises at least one of diffuse reflecting surface light sources, white light sources, light emitting diodes, gas discharge lamps, gas lasers, diode lasers, flash lamps, infrared lamps, glowbars, mercury lamps, and sodium lamps.

5. The apparatus of claim 1, wherein the positioning device is configured to displace the sample stage from an optical path between the detector and the light source to permit spectral measurement of the light source.

6. The apparatus of claim 1, wherein the detector comprises a spectral photodetector configured to wavelength resolve the reflected light from the object.

7. The apparatus of claim 1, wherein the detector is configured to have an angle of acceptance that receives as the reflected light specularly reflected light from the object.

8. The apparatus of claim 1, wherein:
   the front reflecting surface and back reflecting surface of the object are separated by a distance of at least one millimeter, and the light source has substantially uniform irradiance over a diameter to permit collection of multiple surface reflections from the object into the detector.

9. The apparatus of claim 1, wherein the light source comprises an extended angular light source configured to emit light onto the object over an extended range of incident angles.

10. The apparatus of claim 9, wherein the extended range is at least 45 degrees from normal to the object.

11. The apparatus of claim 1, wherein the detector comprises a plurality of detectors arranged at a plurality of angles relative to the object.

12. The apparatus of claim 1, wherein the light source comprises a plurality of light sources arranged at a plurality of angles to the object.

13. The apparatus of claim 1, further comprising:
a diffusing device disposed between the light source and the sample stage, said diffusing device configured to diffuse and randomly polarize light from the light source.

14. The apparatus of claim 1, further comprising:
a depolarizing device disposed between the light source and the sample stage, said depolarizing device configured to randomly polarize light from the light source.

15. The apparatus of claim 1, further comprising:
two depolarizing devices; one disposed between the light source and the sample stage, one of said depolarizing devices configured to randomly polarize light from the light source and another one of said depolarizing devices disposed between the sample and prior to the reflected light being spread into an individual wavelength spectrum.

16. The apparatus of claim 1, further comprising:
at least one shutter disposed between the detector and the sample stage, and configured to permit separate measurements for the respective specular reflectances from the back and front surfaces of the object.

17. The apparatus of claim 1, further comprising:
at least one polarizer disposed on an optical path between the light source and the detector, said polarizer configured to permit separate measurements of the total specular reflectance of the front and back reflecting surfaces of the object in both a plane of polarization in the plane of incidence and a plane of polarization normal to the plane of incidence.

18. The apparatus of claim 1, wherein the light source comprises:
an extended light source configured to provide an extended curved optically diffuse or specularly reflecting device from a single lamp.

19. The apparatus of claim 1, wherein the positioning device comprises:
a goniometer having a ball race configured to move the light source, sample object and detector attached to the goniometer in such a manner that light from the source specularly reflected from the sample object is constantly directed towards the detector as an angle between a first optic axis of the light source and a second optic axis of the detector is varied.

20. The apparatus of claim 1, wherein the detector is configured to collect the reflected light from all surfaces of an insulated glass unit or mockup thereof.

21. The apparatus of claim 1, further comprising:
a computing device configured to compute a ratio of a signal corresponding to the reflected light from the object to a reference signal corresponding to direct light from the source to the detector to provide a radiometric total specular reflectance of the object.

22. The apparatus of claim 1, further comprising:
a computing device configured to compute a ratio of a signal corresponding to the reflected light from the object to a reference signal corresponding to reflected light from a reference surface of known spectral reflectance to provide a radiometric total specular reflectance of the object.

23. The apparatus of claim 1, further comprising:
a computing device configured to receive data from the detector and to calculate at least one of angle dependent spectral reflectance and angular color data from the angular positions and from the wavelength resolution of the reflected light.

24. The apparatus of claim 23, wherein the computing device is configured to provide at least one of the angle dependent spectral reflectance or the angular color data to a process controller for control of a glass manufacturing process.

25. The apparatus of claim 24, wherein the process controller includes artificial intelligence algorithms operating on at least one of the angle dependent spectral reflectance or the angular color data to provide instructions to the glass manufacturing process.

26. An apparatus for measuring reflectance properties of an object, comprising:
a sample stage for placement of the object
a light source
a detector configured to detect reflected light from the object; and
a positioning device configured to at least one of rotate the light source at twice the angular rate as the sample stage while the detector remains fixed or to rotate the detector at twice the angular rate as the sample stage while the light source remains fixed.

27. An apparatus for measuring reflectance properties of an object having a front reflecting surface and a back reflecting surface, comprising:
a sample stage for placement of the object
a light source
a detector configured to detect reflected light from the object; and
a positioning device configured to vary the angle of incidence of the light from the light source on the object and ensure that specularly reflected light from the object is always direct towards the detector as the angle of incidence varies and the reflected light received at the detector includes a front surface reflection from the object and at least one back surface reflection from the object.

28. A method for measuring reflectance properties of an object having a front reflecting surface and at least one back reflecting surface, comprising:
illuminating the object at varying angles of incidence;
collecting reflected light from the front and back reflecting surfaces of the object at respective specularly reflected angles;
wavelength resolving the reflected light into a color spectrum; and
analyzing an intensity of the color spectrum as a function of wavelength.

* * * * *